United States Patent
Stella et al.

(10) Patent No.: US 12,053,539 B2
(45) Date of Patent: Aug. 6, 2024

(54) HAIR CARE COMPOSITIONS COMPRISING HYDROXYLATED TRIGLYCERIDE OLIGOMERS

(71) Applicant: The Procter & Gamble Company, Cincinnati, OH (US)

(72) Inventors: Qing Stella, Cincinnati, OH (US); Kevin Lee Doyle, Fairfield, OH (US); Michael Stephen Maile, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/838,364

(22) Filed: Jun. 13, 2022

(65) Prior Publication Data
US 2022/0401322 A1 Dec. 22, 2022

Related U.S. Application Data

(60) Provisional application No. 63/210,511, filed on Jun. 15, 2021.

(51) Int. Cl.
| | | |
|---|---|---|
| A61K 8/36 | (2006.01) | |
| A61K 8/04 | (2006.01) | |
| A61K 8/41 | (2006.01) | |
| A61Q 5/12 | (2006.01) | |

(52) U.S. Cl.
CPC .............. *A61K 8/361* (2013.01); *A61K 8/042* (2013.01); *A61K 8/416* (2013.01); *A61Q 5/12* (2013.01); *A61K 2800/34* (2013.01); *A61K 2800/5922* (2013.01)

(58) Field of Classification Search
CPC ........ A61K 8/361; A61K 8/042; A61K 8/461; A61K 2800/34; A61K 2800/5922; A61Q 5/12
See application file for complete search history.

(56) References Cited

U.S. PATENT DOCUMENTS

| | | |
|---|---|---|
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,658,072 A | 11/1953 | Milton |
| 2,809,971 A | 10/1957 | Jack et al. |
| 2,826,551 A | 3/1958 | Geen |
| 3,236,733 A | 2/1966 | Karsten et al. |
| 3,753,196 A | 8/1973 | Kurtz et al. |
| 3,761,418 A | 9/1973 | Parran |
| 3,929,678 A | 12/1975 | Laughlin |
| 3,964,500 A | 6/1976 | Drakoff |
| 4,323,683 A | 4/1982 | Bolich, Jr. et al. |
| 4,345,080 A | 8/1982 | Bolich, Jr. |
| 4,364,837 A | 12/1982 | Pader |
| 4,379,753 A | 4/1983 | Bolich, Jr. |
| 4,470,982 A | 9/1984 | Winkler |
| 4,857,310 A | 8/1989 | Baydar |
| 5,104,646 A | 4/1992 | Bolich, Jr. |
| 5,106,609 A | 4/1992 | Bolich, Jr. |
| RE34,584 E | 4/1994 | Grote et al. |
| 6,649,155 B1 | 11/2003 | Dunlop et al. |
| 2006/0099167 A1 | 5/2006 | Staudigel et al. |
| 2008/0206355 A1 | 8/2008 | Schwartz et al. |
| 2008/0317698 A1 | 12/2008 | Wells et al. |
| 2013/0174863 A1* | 7/2013 | Marsh .................... A61K 8/44 132/202 |
| 2013/0280192 A1 | 10/2013 | Carter et al. |
| 2013/0289301 A1 | 10/2013 | Bastioli et al. |
| 2016/0106663 A1 | 4/2016 | Gulbin |

FOREIGN PATENT DOCUMENTS

| | | | |
|---|---|---|---|
| FR | 2931069 A1 | 11/2009 | |
| GB | 849433 A | 9/1960 | |
| JP | 2006052147 A | 2/2006 | |
| JP | 2007039360 A | 2/2007 | |
| JP | 2007126371 A | 5/2007 | |
| JP | 2007238457 A | 9/2007 | |
| JP | 5661252 B2 | 12/2014 | |
| JP | 2018168115 A | 11/2018 | |
| KR | 102013254 B1 | 8/2019 | |
| WO | 9406403 A1 | 3/1994 | |
| WO | 2012012084 A2 | 1/2012 | |
| WO | WO2013158381 A2 * | 10/2013 | ............. A61K 8/342 |

OTHER PUBLICATIONS

English Translation of FR2931069A1, Pub. Date: Nov. 2009 (Year: 2009).*
16056 PCT Search Report and Written Opinion forPCT/US2022/033540 dated Nov. 4, 2022, 10 pages.

* cited by examiner

*Primary Examiner* — Genevieve S Alley
(74) *Attorney, Agent, or Firm* — John G. Powell; Kathleen Y. Carter

(57) ABSTRACT

Disclosed are hair care compositions, such as shampoos, conditioners and leave on treatments, containing one or more hydroxylated triglyceride oligomers. Also disclosed are methods of using the hair care compositions.

18 Claims, 12 Drawing Sheets with $R_1 =$ approx. 75% and approx. 25% and $R_2 =$ with R₁ = and R₂ = with $R_1 =$ and $R_2 =$ with R₁ = and R₂ = and R₃ = having four anionic counter ions Cl⁻ and
two anionic counter ions with $R_1 =$ and with $R_2 =$ having four anionic counter ions Cl⁻ and two anionic counter ions with $R_1$ = and with $R_2$ = with R₁ (linking to two of the above R₂ containing elements) = having two anionic counter ions and with R₂ =

The formed sodium chloride precipitates upon storage.

with R = -C(O)CH₃

HAIR CARE COMPOSITIONS COMPRISING HYDROXYLATED TRIGLYCERIDE OLIGOMERS

FIELD OF THE INVENTION

The present invention relates to a hair care composition containing a hydroxylated triglyceride oligomer derived from castor oil or lesquerella oil, and methods of using the same.

BACKGROUND OF THE INVENTION

Human hair becomes soiled due to its contact with the surrounding environment and from the sebum secreted by the scalp. The soiling of hair causes it to have a dirty feel and an unattractive appearance.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils.

A variety of approaches have been developed to alleviate these after-shampoo problems. One approach is the application of hair shampoos which attempt to both cleanse and condition the hair from a single product. Other approaches include the applications of hair conditioner and/or a leave in treatment following shampooing.

In order to provide hair conditioning benefits in a hair care base, a wide variety of conditioning actives have been proposed. However, including active levels of conditioning agents in shampoos, conditioners and treatments may result in rheology and stability issues, creating consumer trade-offs in cleaning, lather profiles, and weigh-down effects. Additionally, the rising costs of silicone and the non-biodegradable nature of silicone have minimized silicone's desirability as a conditioning active.

Based on the foregoing, there is a need for a conditioning active which can provide conditioning benefits to hair and can replace, or be used in combination with silicone, or other conditioning actives, to maximize the conditioning activity of hair care compositions. Additionally, there is a desire to find a conditioning active which can be derived from a natural source, thereby providing a conditioning active derived from a renewable resource. There is also a desire to find a conditioning active that is both biodegradable and leads to a stable product comprising a micellar surfactant system.

SUMMARY OF THE INVENTION

The present invention is directed to a hair care composition comprising:
  a) from about 0.01% to about 15%, by weight of said hair care composition, of a hydroxylated triglyceride oligomer comprising:
    (i.) at least two hydroxylated triglyceride repeating units, wherein the hydroxylated triglyceride repeating units comprise one or more hydroxyl groups; and
    (ii.) at least one fatty acid esterified with at least one of the hydroxyl groups in the hydroxylated triglyceride oligomer, and
    wherein the oligomer has a viscosity of from 1 to 30 Pa·s; and
  b) a vehicle having one or more of the following components, by weight of said hair care composition,
    (i.) an aqueous carrier;
    (ii.) from about 5% to about 50% of one or more anionic surfactants in an aqueous carrier;
    (ii.) a gel matrix phase in an aqueous carrier comprising, by weight of said hair care composition:
      1) from about 0.1% to about 20% of one or more high melting point fatty compounds;
      2) from about 0.1% to about 10% of a cationic surfactant system;
    (iii.) from about 0.1% to 20% of a nonionic surfactant in an aqueous carrier;
    (iv.) from about 20% to about 99.99% of a solvent carrier.

The present invention also is directed to a method for cleansing and conditioning hair with an effective amount of the hair care composition described above.

These and other features, aspects, and advantages of the present invention will become evident to those skilled in the art from a reading of the present disclosure.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be non-limiting and are understood to mean "comprise," "comprises," and "comprising," respectively.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. The term "weight percent" may be denoted as "wt. %" herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Figure 1:
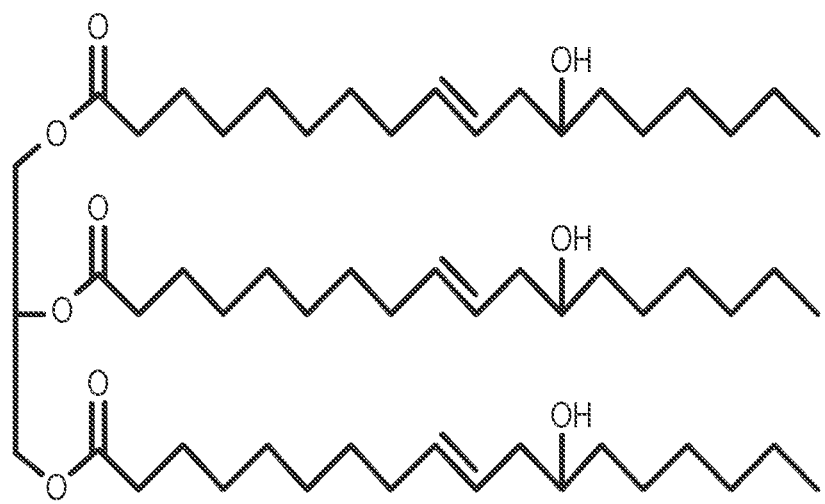
FIG. 1 shows the structure of castor oil.
Figure 2:
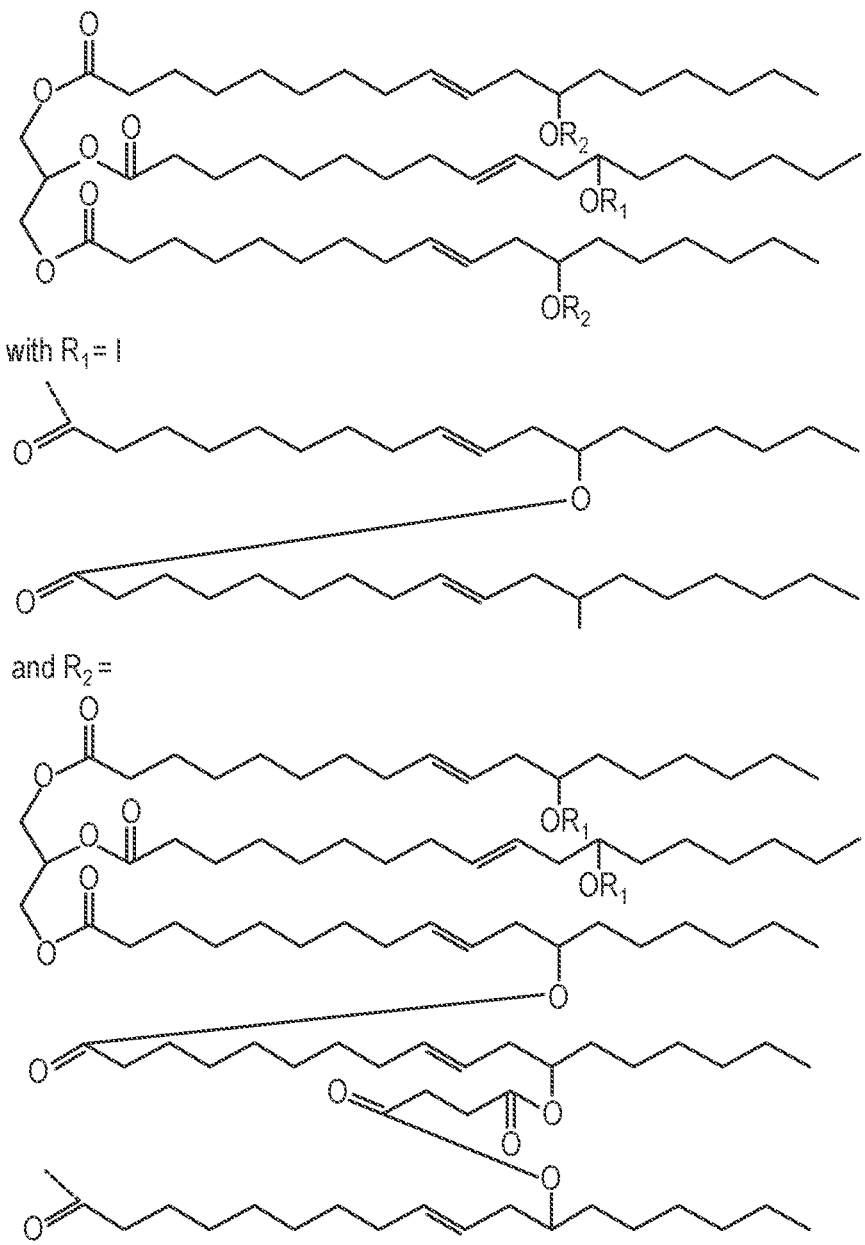
FIGS. 2-9 show structures of Materials 1-8, respectively, used in inventive compositions.
Figure 3:
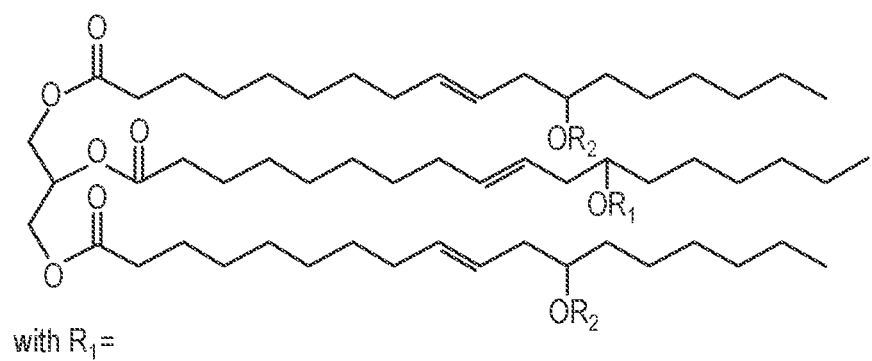
Figure 3:
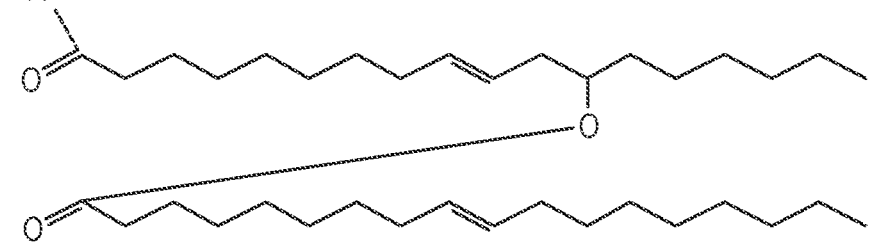
Figure 3:
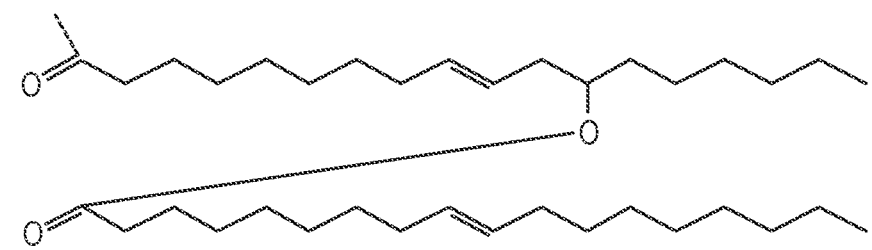
Figure 3:
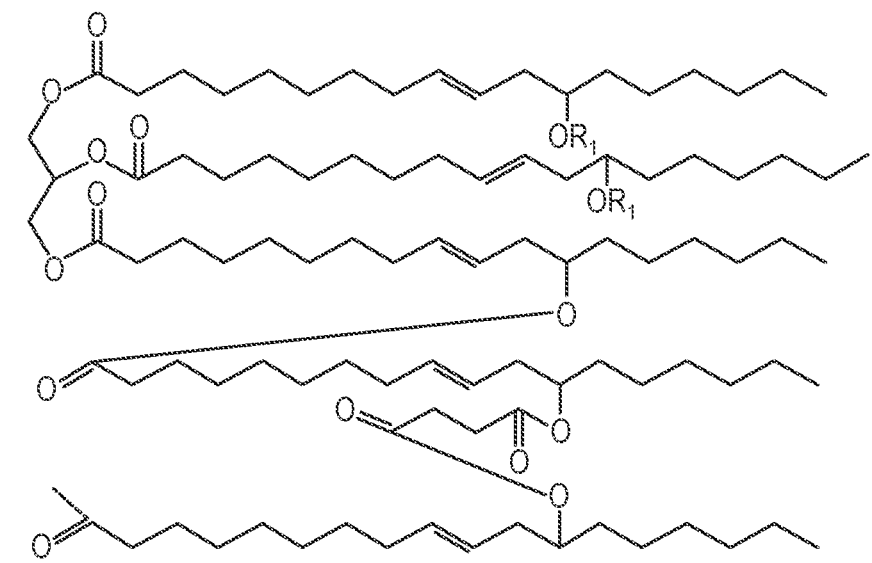
Figure 4:
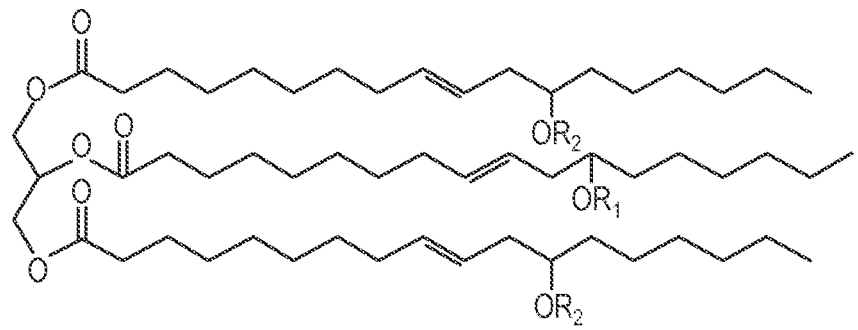
Figure 4:
Figure 4:
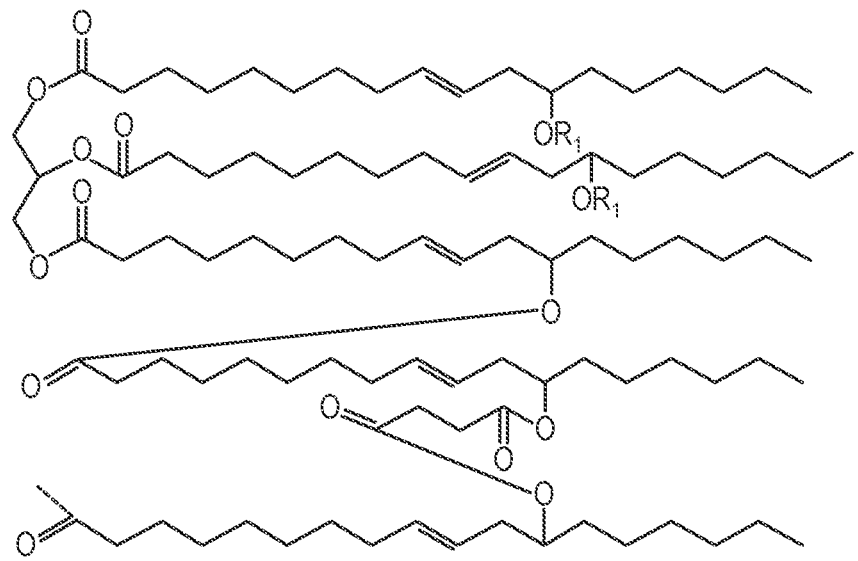
Figure 5:
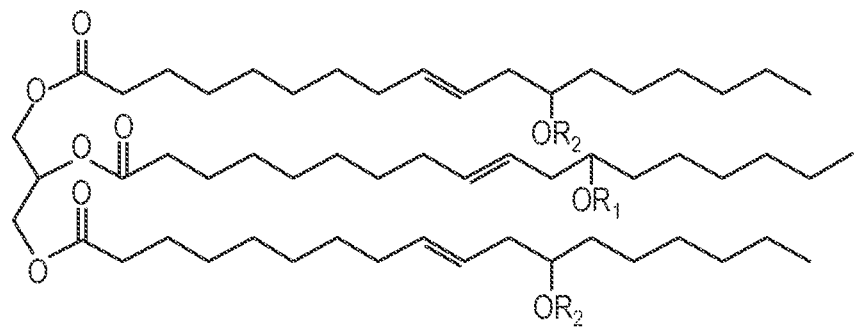
Figure 5:
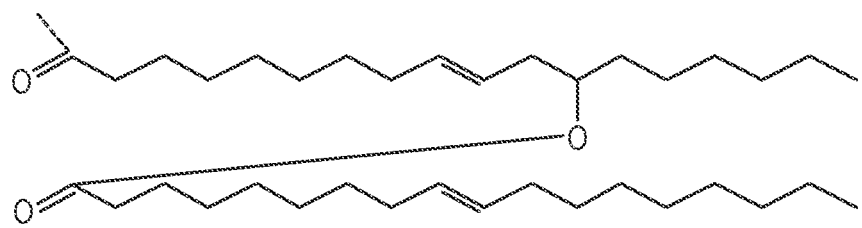
Figure 5:
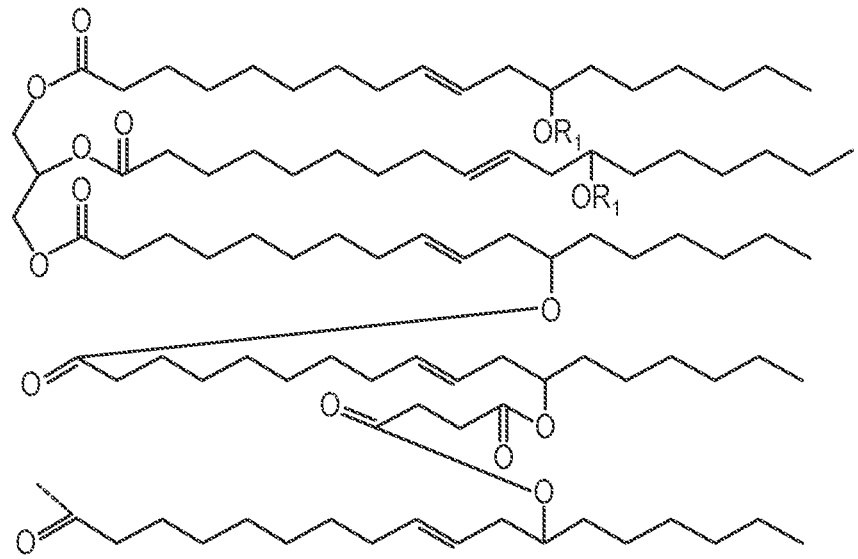
Figure 6:
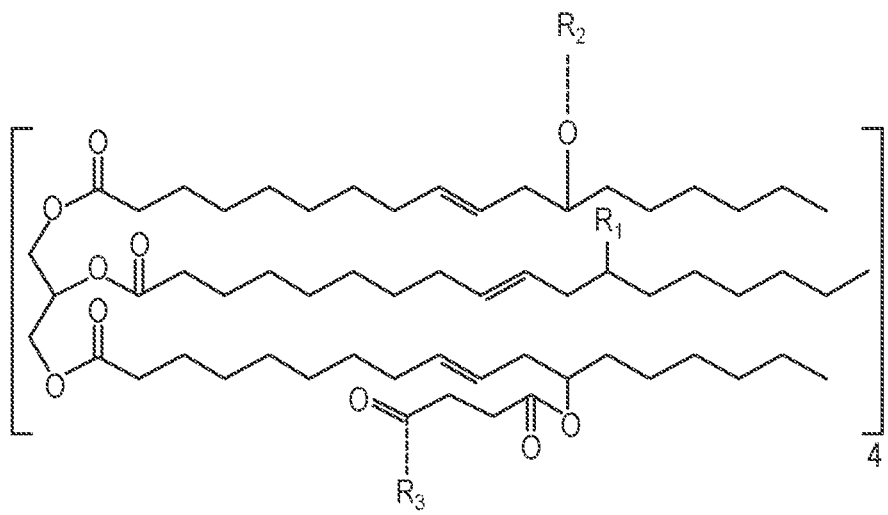
Figure 6:
Figure 6:
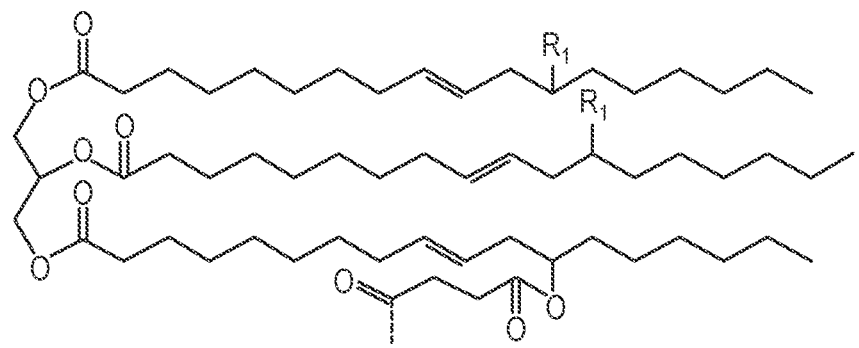
Figure 6:
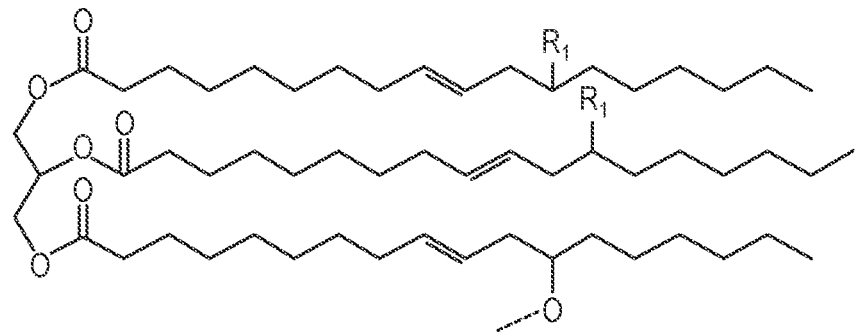

A. Hydroxylated Triglyceride Oligimers Derived from Castor Oil or Lesquerella Oil The hair care composition may comprise from about 0.01% to about 15%, alternatively from about 0.1% to about 10%, and alternatively from about 0.25% to about 5%, of one or more derivatives of castor oil, specifically oligomers derived from castor oil (ricinoleic triglyceride oligomers) and lesquerella oil (lesquerolic triglyceride oligomers) by weight of said hair care composition. The term "derivatives" means the resulting esters of an esterification reaction of the hydroxyl groups contained in castor or lesquerella oil, wherein the esters are derived from carboxylic acids or functional carboxylic acids, and the resulting materials are nonionic or cationic in nature. The structure of castor oil is shown in FIG. 1.

Exemplary hydroxylated triglyceride oligomers and their preparation methods are set forth herein. A hydroxylated triglyceride oligomer refers to the product obtained when more than one ricinoleic triglyceride is subjected to an esterification reaction. Esterification is a reaction of an alcohol with an acid to produce an ester and water. When the acid is a diacid, the propagation of the ester linkage may occur resulting in oligomerization or polymerization of the hydroxylated triglyceride. For example, the structures of Materials 1-5, as shown in FIGS. 2-6, depict hydroxylated triglyceride oligomers comprising ricinoleic triglyceride and succinic acid. In these structures, the esterification results in the formation of hydroxylated triglyceride oligomers. The molecular weight of the oligomer determined by Gel Permeation Chromatography (GPC) using polystyrene as standard may be higher than the molecular weight of the hydroxylated triglyceride from which the oligomer is formed. Each of the bonded hydroxylated triglyceride ester molecules may be referred to as a "repeating unit or group". Typically, the number of hydroxylated triglyceride repeat units may range from 2 to about 6. In many embodiments of the invention, the ricinoleic triglyceride is further esterified with a hydroxylated fatty acid. Examples of the hydroxylated fatty acid include ricinoleic acid and 12-hydroxy stearic acid. The purpose of the additional hydroxylated fatty acid ester on ricinoleic triglyceride is twofold. First, the hydroxyl group on the hydroxylated acid ester serves as the reaction site for the esterification with succinic acid. The resulting hydroxylated triglyceride oligomer has a longer linker containing two hydroxylated fatty acid groups and one succinic group between the ricinoleic triglyceride repeating units than the linker of the hydroxylated triglyceride oligomers formed directly by ricinoleic triglyceride and succinic acid. A shorter linker has only succinic group between the ricinoleic triglyceride repeating units. The long linker examples of hydroxylated triglyceride oligomers include Material 1, Material 2, Material 3, and Material 4, while an example of short linker is Material 5. The linker length is thought to affect molecular flexibility of the oligomers. A long linker is likely to reduce molecular steric hindrance, resulting in more extended conformation of the hydroxylated triglyceride oligomer than a short linker. Second, the additional hydroxylated fatty acid ester on ricinoleic triglyceride, which is not used for the reaction with the diacid, can be further esterified with fatty acids to extend the ricinoleic group on the hydroxylated triglyceride oligomer. The fatty acids may include stearic acid, oleic acid, 12-hydroxy acid and mixtures thereof. In some embodiments, the materials may comprise some residual non-esterified fatty acid, which can form a separate gel-like phase with or in the oligomer. An exemplary material is Material 1. The examples of Material 3, Material 4, and Material 5 have oleic acid ester. The example of Material 1 has stearic acid ester. The example of Material 2 has a mixture of stearic acid ester of 25 wt % and oleic acid ester of 75 wt %. In some embodiments, the residual fatty acid may remain in the hydroxylated triglyceride oligomer up to 5 wt %.

Figure 7:
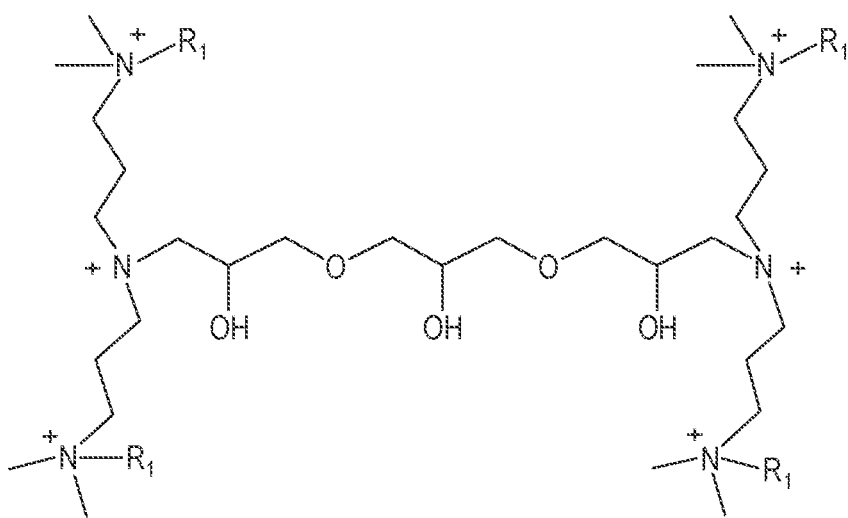
Figure 7:
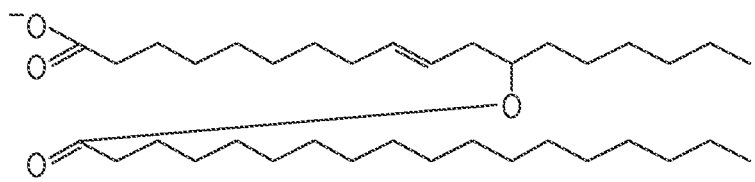
Figure 7:
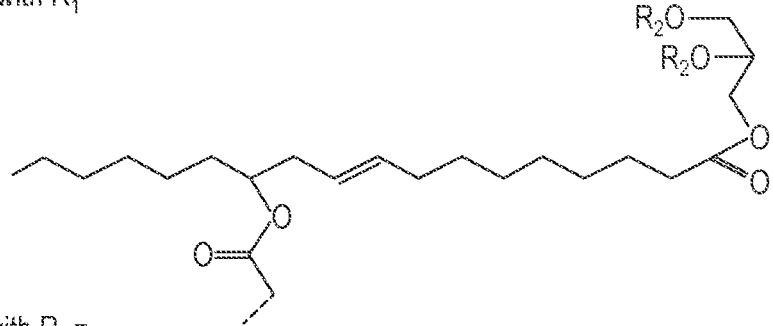
Figure 7:
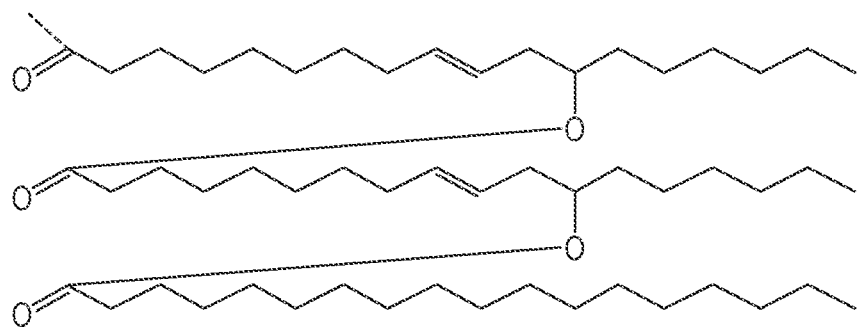
Figure 8:
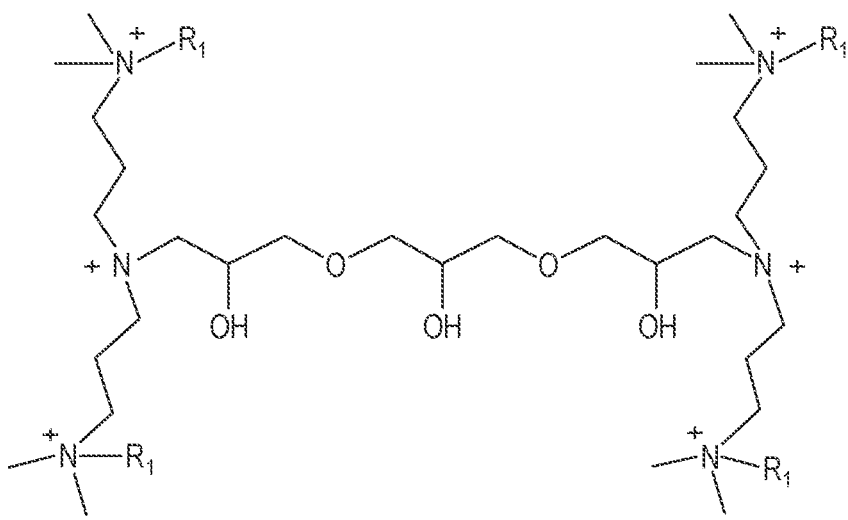
Figure 8:
Figure 8:
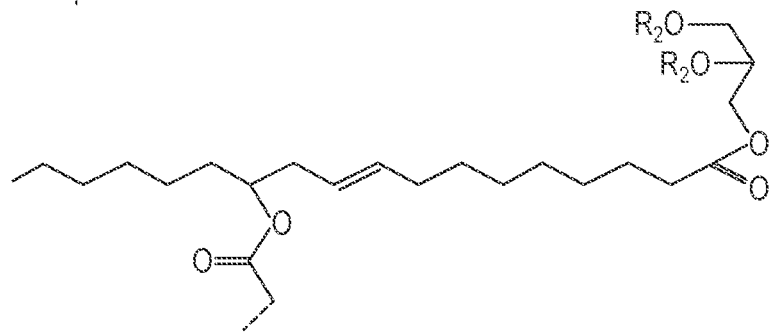
Figure 8:
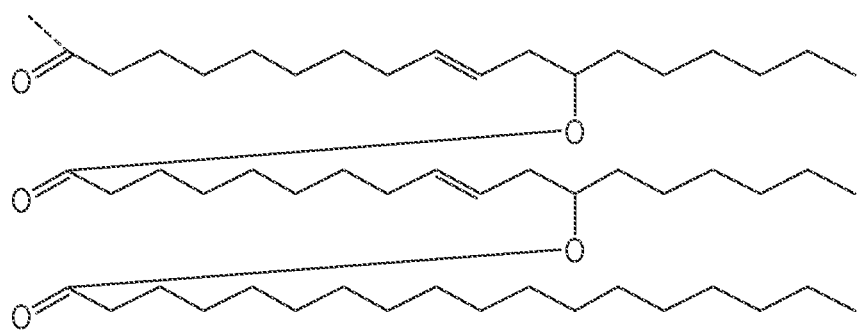
Figure 9:
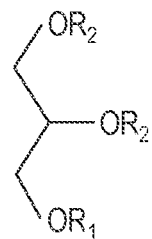
Figure 9:
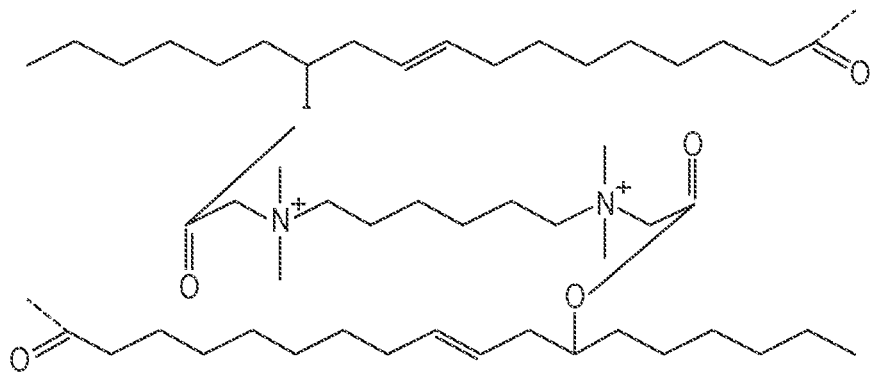
Figure 9:
Figure 9:
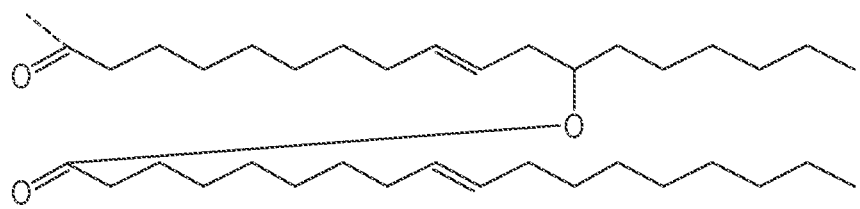

Exemplary cationic hydroxylated triglyceride oligomers and their preparation methods are set forth herein. The cationic hydroxylated triglyceride oligomers may have at least one quaternary ammonium group. The quaternary ammonium group may be from a protonated amino group when formulated in a hair care composition. The cationic hydroxylated triglyceride oligomer may comprise from 2 to about 6 quaternary ammonium groups, as exemplified by Materials 6-8, as shown in FIGS. 7-9, respectively. The quaternary ammonium groups are connected with hydrocarbons such as in Material 8, or with hydroxylated polyethers such as in Material 6 and Material 7. The quaternary ammonium group in the oligomer may have a counterion, and the counterion may be a chloride or a fatty acid. The fatty acid counterion may be selected from stearic acid, oleic acid, or mixtures thereof. The ricinoleic triglyceride may be linked to the quaternary ammonium group. The cationic hydroxylated triglyceride oligomer may comprise two hydroxylated triglyceride repeating units such as Material 8, or four hydroxylated triglyceride repeating units such as in Materials 6 and 7.

Examples of molecular information for some of the Materials are shown in the table below. The molecular weight was measured via standard Gel Permeation Chromatography (GPC), compared to polystyrene standards.

TABLE 1

|  | Material 3 | Material 5 | Material 1 | Material 7 |
| --- | --- | --- | --- | --- |
| Weight average molecular weight (Mw, Dalton) | 7100 | 11700 | 10200 | 4000 |
| Polydispersity index | 1.42 | 2.61 | 1.99 | 1.4 |
| Wt % of content < Mw 1000 | 3.9 | 1.3 | 1.6 | 4.6 |

In some embodiments, the oligomer may have a viscosity of from about 1 to about 30 Pa·s. In other embodiments, the viscosity may be from about 2 to about 25 Pa·s.

Figure 10:
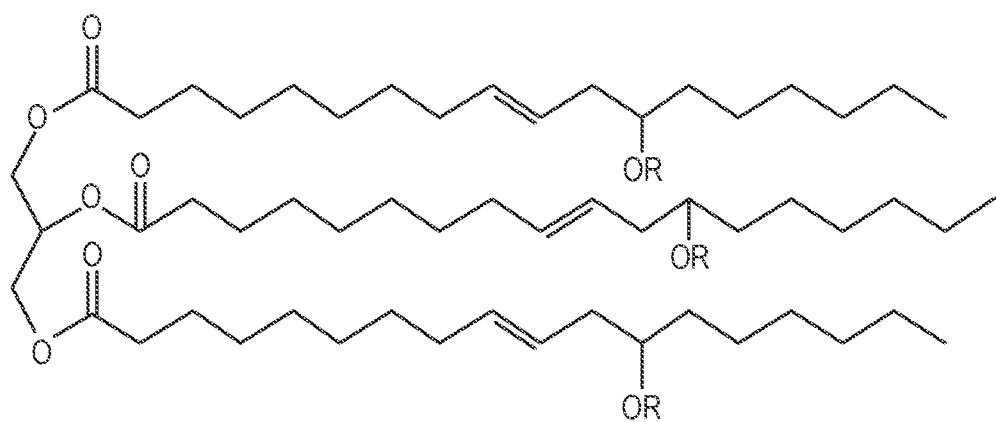
FIGS. 10-12 show structures of Materials 9-11, respectively, used in comparative compositions.
Figure 11:
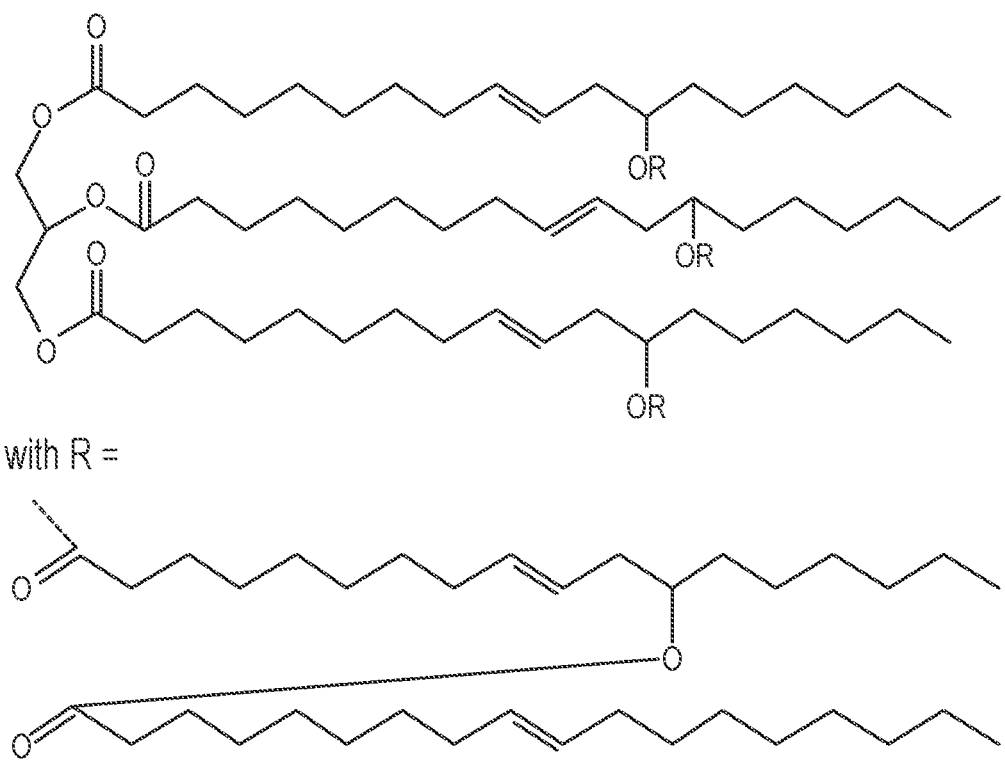

Comparative examples of Material 9 and Material 10 of hydroxylated triglycerides and their preparation methods are set forth herein and shown in FIGS. 10 and 11, respectively.

These examples fail to show the oligomerization of hydroxylated triglyceride, although esterification is achieved with the hydroxyl group on the ricinoleic triglyceride with acetic acid in Material 9 or a fatty acid in Material 10. The viscosity of these examples is below the inventive range of 1 to 30 Pa·s., as shown in Comparative examples A and B.

Figure 12:
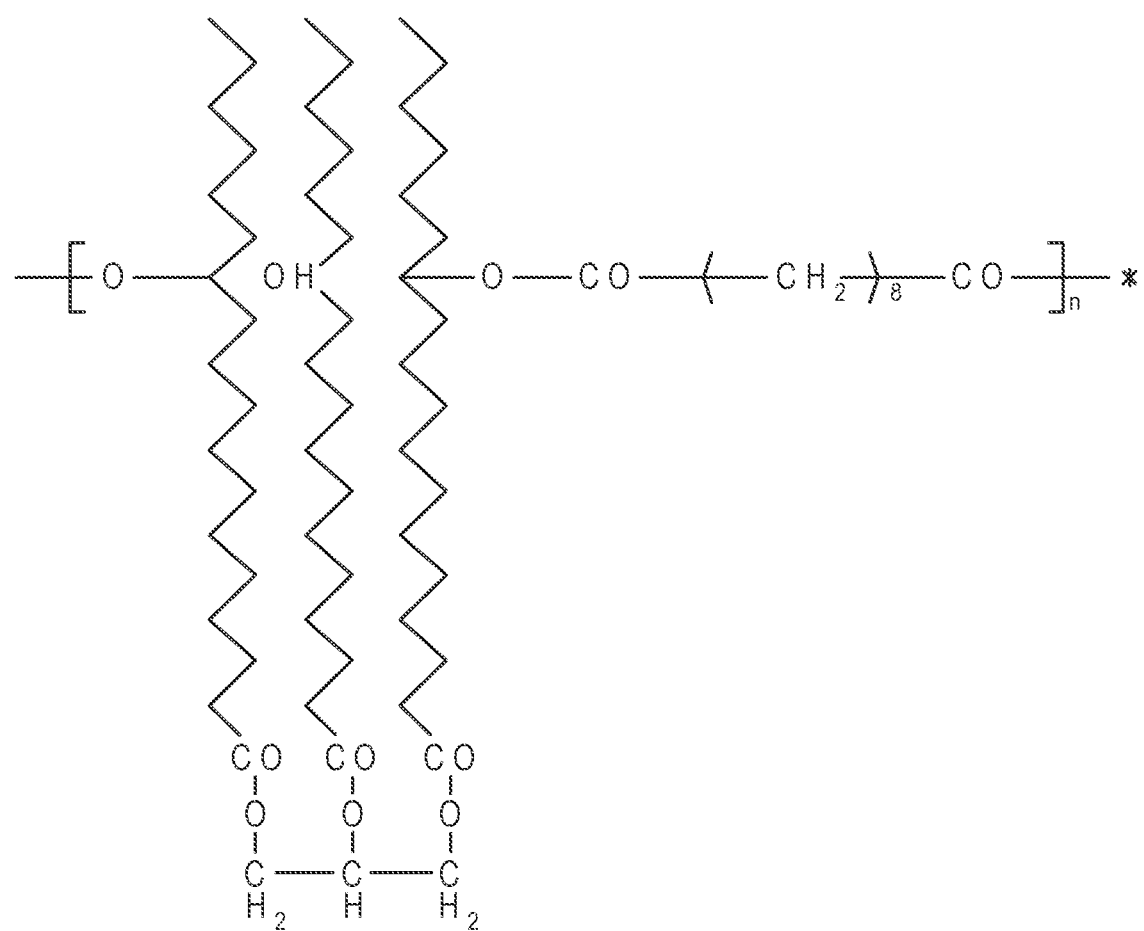

Another comparative example is Material 11, Crodabond CSA from Croda, as shown in FIG. 12. It is a copolymer of Hydrogenated Castor Oil/Sebacic Acid Copolymer, described in detail in Crodabond CSA technical information from Croda and JP2007126371A. Hydrogenated castor oil significantly increases the viscosity of the copolymer to above the high end of the inventive range of 30 Pa·s. for hair conditioning, as shown in Comparative example C. No comparative examples of cationic hydroxylated triglyceride oligomers were found.

The hair care compositions of the present invention may comprise a hydroxylated triglyceride oligomer and a vehicle. The vehicle may comprise combinations of additional components that make up a hair care composition including, without being limited to, a surfactant, emulsifier, a fatty compound, an aqueous carrier, a solvent carrier, and additional components.

B. Surfactant and Emulsifier

The hair care composition may comprise a detersive surfactant, which provides cleaning performance to the composition. The detersive surfactant in turn comprises an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the hair care composition should be sufficient to provide the desired cleaning and lather performance, and generally ranges from about 2 wt % to about 50 wt %, from about 5 wt % to about 30 wt %, from about 8 wt % to about 25 wt %, or from about 10 wt % to about 20 wt %. Accordingly, the hair care composition may comprise a detersive surfactant in an amount of about 5 wt %, about 10 wt %, about 12 wt %, about 15 wt %, about 17 wt %, about 18 wt %, or about 20 wt %, for example.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the hair care composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

A variety of anionic emulsifiers can be used in the hair care composition as described below. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonatc, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar, semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the instant shampoo compositions. Anionic emulsifiers useful herein include, but aren't limited to: poly(meth)acrylic acid; copolymers of (meth) acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer, Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

Suitable amphoteric or zwitterionic surfactants for use in the hair care composition herein include those which are known for use in hair care or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

Zwitterionic detersive surfactants suitable for use in the hair care composition include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The composition of the present invention may comprise a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system may be included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

wherein one of $R^{75}$, $R^{76}$, $R^{77}$ and $R^{72}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Guaternized Ammonium Salt

Di-long alkyl quaternized ammonium salt is preferably combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

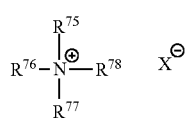

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

The compositions of the present invention may comprise a nonionic surfactant. Suitable nonionic surfactants for use in the hair care compositions include, but are not limited to, the non-ionic detersive surfactant comprises a $C_8$-$C_{24}$ alkyl alkoxylated alcohol having an average degree of alkoxylation of from 1 to 20, preferably a $C_{10}$-$C_{18}$ alkyl alkoxylated alcohol having an average degree of alkoxylation of from 1 to 10, or even a $C_{12}$-$C_{18}$ alkyl alkoxylated alcohol having an average degree of alkoxylation of from 1 to 7. Preferably, the non-ionic detersive surfactant is an ethoxylated alcohol. Preferably, the non-ionic surfactant comprises an alkyl polyglucoside. The non-ionic detersive surfactant may even be a predominantly $C_{16}$ alkyl ethoxylated alcohol having an average degree of ethoxylation of from 3 to 7.

In an embodiment, the surfactant may be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide. PEG-4 Cocamide. PEG-5 Cocamide, PE-6 Cocamide, PEG-7 Cocamide, PEG-3 Lauramide, PEG-5 Lauramide, PEG-3 Oleamide, PPG-2 Cocamide. PPG-2 Hydroxyethyl Cocamide, and mixtures thereof.

Suitable nonionic surfactants for use in the hair care compositions include, but are not limited to, polyoxyethylenated alkyl phenols, polyoxyethylenated alcohols, polyoxyethylenated polyoxypropylene glycols. polyoxyethylenated hydrogenated castor oil. glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylanine oxides, and polyoxyethylenated silicones.

C. High Melting Point Fatty Compound

The high melting point fatty compound that is useful herein may have a melting point of 25° C. or higher and may be selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992. Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 0.1% to about 20%, preferably from about 1% to about 15%, more preferably from about 1.5% to about 8% by weight of the composition, in view of providing improved conditioning benefits such as slippery feel during the application to wet hair, softness and moisturized feel on dry hair.

D. Gel Matrix

The compositions of the present invention may comprise a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

The gel matrix of the hair care composition of the present invention may include an aqueous carrier. Accordingly, the formulations of the present invention can be in the form of pourable liquids (under ambient conditions). Such compositions will therefore typically comprise an aqueous carrier, which is present at a level of from about 20 wt % to about 95 wt %, or even from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

According to embodiments of the present invention, the hair care compositions may have a pH in the range from about 2 to about 10, at 25° C. In one embodiment, the hair care composition has a pH in the range from about 2 to about 6, which may help to solubilize minerals and redox metals already deposited on the hair. Thus, the hair care composition can also be effective toward washing out the existing minerals and redox metals deposits, which can reduce cuticle distortion and thereby reduce cuticle chipping and damage.

E. Aqueous Carrier The hair care compositions can be in the form of pourable liquids (under ambient conditions). Such compositions will therefore typically comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other components.

The carrier useful in embodiments of the hair care composition includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

F. Solvent Carrier

The composition according to the invention can be formulated in an alcoholic or aqueous-alcoholic composition. The hair treating composition can therefore optionally include liquid water-miscible or water-soluble solvents such as lower alkyl alcohols, e. g. $C_1$-$C_5$ alkyl monohydric alcohols, preferably $C_2$-$C_3$ alkyl alcohols. Alcohols which may be present are in particular lower monohydric or polyhydric alcohols having 1 to 4 carbon atoms customarily used for cosmetic purposes, such as preferably ethanol and isopropanol.

The water-soluble polyhydric alcohols usable in the present invention are also polyhydric alcohols having two or more hydroxyl groups in the molecule. Typical examples of such polyhydric alcohols are dihydric alcohols such as ethylene glycol, propylene glycol, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerine, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerine monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurfuryl alcohol, POE tetrahydrofurfuryl alcohol, POP butyl ether, POP POE butyl ether, tripolyoxypropylene glycerine ether, POP glycerine ether, POP glycerine ether phosphoric acid, POP POE pentanerythritol ether.

Additional solvent carriers which may be present are cosmetically acceptable organic solvents or a mixture of solvents with a boiling point below 400° C. Particularly suitable solvent carriers are unbranched or branched hydrocarbons, such as pentane, hexane, isopentane and cyclic hydrocarbons, such as cyclopentane and cyclohexane. Suitable solvent carriers also include cyclomethicones, such as cyclopentasiloxane.

G. Additional Components

The hair care composition may further comprise one or more additional components known for use in hair care or personal care products, provided that the additional components do not otherwise unduly impair product stability, aesthetics, or performance. Such optional ingredients are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the personal care compositions.

Non-limiting examples of additional components for use in the hair care composition include conditioning agents (e.g., silicones, hydrocarbon oils, fatty esters, natural oils), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

In one embodiment, the hair care compositions comprise one or more conditioning agents. Conditioning agents include materials that are used to give a particular conditioning benefit to hair and/or skin. The conditioning agents useful in the hair care compositions typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01 wt % to about 10 wt %, alternatively from about 0.1 wt % to about 8 wt %, and alternatively from about 0.2 wt % to about 4 wt %, by weight of the composition.

a. Silicones

The conditioning agent of the hair care composition may be an insoluble silicone conditioning agent. The silicone conditioning agent particles may comprise volatile silicone, non-volatile silicone, or combinations thereof. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, by weight of the composition, alternatively from about 0.1% to about 8%, alternatively from about 0.1% to about 5%, and alternatively from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the hair care composition may have a viscosity, as measured at 25Å° C., from about 20 to about 2,000,000 centistokes ("csk"), alternatively from about 1,000 to about 1,800,000 csk, alternatively from about 50,000 to about 1,500,000 csk, and alternatively from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, alternatively from about 0.01 micrometer to about 2 micrometer, and alternatively from about 0.01 micrometer to about 0.5 micrometer. For larger particle application to hair, the volume average particle diameters typically range from about 5 micrometer to about 125 micrometer, alternatively from about 10 micrometer to about 90 micrometer, alternatively from about 15 micrometer to about 70 micrometer, and alternatively from about 20 micrometer to about 50 micrometer.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

i. Silicone Oils

Silicone fluids include silicone oils, which are flowable silicone materials having a viscosity, as measured at 25° C., less than 1,000,000 csk, alternatively from about 5 csk to about 1,000,000 csk, and alternatively from about 100 csk to about 600,000 csk. Suitable silicone oils for use in the hair care composition include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (I):

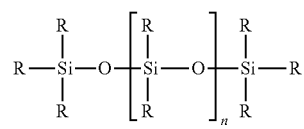

wherein R is aliphatic, in some embodiments alkyl, alkenyl, or aryl, R can be substituted or unsubstituted, and x is an integer from 1 to about 8,000. Suitable R groups for use in the compositions include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Possible alkyl and alkenyl substituents include $C_1$ to $C_5$ alkyls and alkenyls, alternatively from $C_1$ to $C_4$, and alternatively from $C_1$ to $C_2$. The aliphatic portions of other alkyl-, alkenyl-, or alkynyl-containing groups (such as alkoxy, alkaryl, and alkamino) can be straight or branched chains, and may be from $C_1$ to $C_5$, alternatively from $C_1$ to $C_4$, alternatively from $C_1$ to $C_3$, and alternatively from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length may be as described herein.

ii. Amino and Cationic Silicones

Cationic silicone fluids suitable for use in the compositions include, but are not limited to, those which conform to the general formula (II):

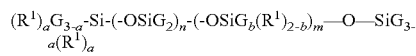

wherein G is hydrogen, phenyl, hydroxy, or $C_1$-$C_8$ alkyl, in some embodiments, methyl; a is 0 or an integer having a value from 1 to 3; b is 0 or 1; n is a number from 0 to 1,999, alternatively from 49 to 499; m is an integer from 1 to 2,000, alternatively from 1 to 10; the sum of n and m is a number from 1 to 2,000, alternatively from 50 to 500; $R^1$ is a monovalent radical conforming to the general formula $CqH_{2q}L$, wherein q is an integer having a value from 2 to 8 and L is selected from the following groups:
—$N(R^2)CH_2$—$CH_2$—$N(R^2)_2$
—$N(R^2)_2$
—$N(R^2)_3$ $A^-$
—$N(R^2)CH_2$—$CH_2$—$NR^2H_2$ $A^-$
wherein $R^2$ is hydrogen, phenyl, benzyl, or a saturated hydrocarbon radical, in some embodiments an alkyl radical from about $C_1$ to about $C_{20}$, and $A^-$ is a halide ion.

In one embodiment, the cationic silicone corresponding to formula (II) is the polymer known as "trimethylsilylamodimethicone", which is shown below in formula (III):

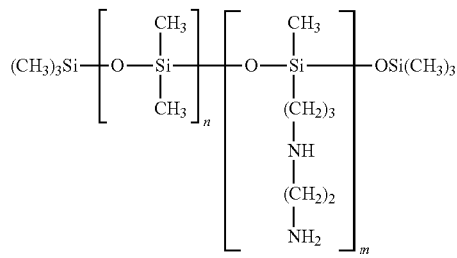

Other silicone cationic polymers which may be used in the hair care composition are represented by the general formula (IV):

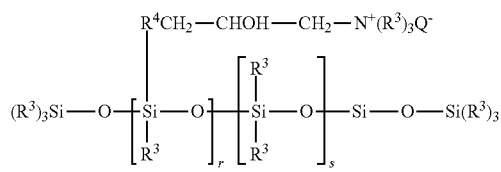

wherein $R^3$ is a monovalent hydrocarbon radical from $C_1$ to $C_{18}$, in some embodiments an alkyl or alkenyl radical, such as methyl; $R_4$ is a hydrocarbon radical, in some embodiments a $C_1$ to $C_{18}$ alkylene radical or a $C_{10}$ to $C_{18}$ alkyleneoxy radical, alternatively a $C_1$ to $C_8$ alkyleneoxy radical; $Q^-$ is a halide ion, in some embodiments chloride; r is an average statistical value from 2 to 20, in some embodiments from 2 to 8; s is an average statistical value from 20 to 200, in some embodiments from 20 to 50. One polymer of this class is known as UCARE SILICONE ALE 56@, available from Union Carbide.

iii. Silicone Gums

Other silicone fluids suitable for use in the hair care composition are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, Chemistry and Technology of Silicones, New York: Academic Press (1968); and in General Electric Silicone Rubber Product Data Sheets SE 30, SE 33, SE 54 and SE 76, all of which are incorporated herein by reference. Specific non-limiting examples of silicone gums for use in the hair care include polydimethylsiloxane, (polydimethylsiloxanexmethylvinylsiloxane)copolymer, poly(dimethylsiloxanexdiphenyl siloxanexmethylvinylsiloxane)copolymer and mixtures thereof.

iv. High Refractive Index Silicones

Other non-volatile, insoluble silicone fluid conditioning agents that are suitable for use in the hair care composition are those known as "high refractive index silicones," having a refractive index of at least about 1.46, alternatively at least about 1.48, alternatively at least about 1.52, and alternatively at least about 1.55. The refractive index of the polysiloxane fluid will generally be less than about 1.70, typically less than about 1.60. In this context, polysiloxane "fluid" includes oils as well as gums. The high refractive index polysiloxane fluid includes those represented by general Formula (I) above, as well as cyclic polysiloxanes such as those represented by Formula (V) below:

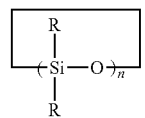

wherein R is as defined above, and n is a number from about 3 to about 7, alternatively from about 3 to about 5.

The high refractive index polysiloxane fluids contain an amount of aryl-containing R substituents sufficient to increase the refractive index to the desired level, which is described herein. Additionally, R and n may be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, alternatively at least about 20%, alternatively at least about 25%, alternatively at least about 35%, and alternatively at least about 50%. Typically, the degree of aryl substitution will be less than about 90%, more generally less than about 85%, alternatively from about 55% to about 80%. In some embodiments, the high refractive index polysiloxane fluids have a combination of phenyl or phenyl derivative substituents, with alkyl substituents, in some embodiments $C_1$-$C_4$ alkyl, hydroxy, or $C_1$-$C_4$ alkylamino (especially -$R^4NHR^5NH_2$ wherein each $R^4$ and $R^5$ independently is a $C_1$-$C_3$ alkyl, alkenyl, and/or alkoxy).

When high refractive index silicones are used in the hair care composition, they may be used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the hair care composition are disclosed in U.S. Pat. Nos. 2,826,551, 3,964,500, 4,364,837, British Pat. No. 849,433, and Silicon Compounds, Petrarch Systems, Inc. (1984), all of which are incorporated herein by reference.

v. Silicone Resins

Silicone resins may be included in the silicone conditioning agent of the hair care composition. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Silicone resins for use in the hair care composition may include, but are not limited to MQ, MT, MTQ, MDT and MDTQ resins. Methyl is a possible silicone substituent. In some embodiments, silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, may be from about 4:1 to about 400:1, alternatively from about 9:1 to about 200:1, and alternatively from about 19:1 to about 100:1, particularly when the silicone fluid component is a polydimethylsiloxane fluid or a mixture of polydimethylsiloxane fluid and polydimethylsiloxane gum as described herein. Insofar as the silicone resin forms a part of the same phase in the compositions hereof as the silicone fluid, i.e. the conditioning active, the sum of the fluid and resin should be included in determining the level of silicone conditioning agent in the composition.

b. Organic Conditioning Oils

The conditioning agent of the hair care hair care composition may also comprise at least one organic conditioning oil, either alone or in combination with other conditioning agents, such as the silicones described above.

i. Hydrocarbon Oils

Suitable organic conditioning oils for use as conditioning agents in the hair care composition include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils may be from about $C_{12}$ to about $C_{19}$. Branched chain hydrocarbon oils, including hydrocarbon polymers, typically will contain more than 19 carbon atoms.

ii. Polyolefins

Organic conditioning oils for use in the hair care composition can also include liquid polyolefins, alternatively liquid poly-α-olefins, alternatively hydrogenated liquid poly-(α-olefins. Polyolefins for use herein are prepared by polymerization of $C_4$ to about $C_{14}$ olefenic monomers, in some embodiments from about $C_6$ to about $C_{12}$.

iii. Fatty Esters

Other suitable organic conditioning oils for use as the conditioning agent in the hair care hair care composition include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

iv. Fluorinated Conditioning Compounds

Fluorinated compounds suitable for delivering conditioning to hair or skin as organic conditioning oils include perfluoropolyethers, perfluorinated olefins, fluorinebased specialty polymers that may be in a fluid or elastomer form similar to the silicone fluids previously described, and perfluorinated dimethicones.

v. Fatty Alcohols

Other suitable organic conditioning oils for use in the personal care hair care composition include, but are not limited to, fatty alcohols having at least about 10 carbon atoms, alternatively from about 10 to about 22 carbon atoms, and alternatively from about 12 to about 16 carbon atoms.

vi. Alkyl Glucosides and Alkyl Glucoside Derivatives

Suitable organic conditioning oils for use in the personal care hair care composition include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

vii. Natural Oils

Natural oils of the type described herein typically are composed of triglycerides and esters of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a $C_{16}$ acid), and oleic acid (a $C_{18}$ acid); polyunsaturated acids include such fatty acids as linoleic acid (a di-unsaturated $C_{18}$ acid), linolenic acid (a tri-unsaturated $C_{18}$ acid), and arachidonic acid (a tetra-unsubstituted $C_{20}$ acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example, soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of oil. Therefore, for soybean oil, the average iodine value range is from 120-140. Soybean oil may comprises about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12octadecadienoic acid), and linolenic acid (9,12,15-octadecatrienoic acid).

In an exemplary embodiment, the vegetable oils include, but not limited to, canola oil, safflower oil, argan oil, jojoba oil, coconut oil, shea butter, orange peel wax, tea tree oil, rice bran oil.

c. Other Conditioning Agents i. Quaternary Ammonium Compounds

Suitable quaternary ammonium compounds for use as conditioning agents in the personal care hair care composition include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

iii. Cationic Polymers

The personal care composition may further comprise a cationic polymer. In combination with a cationic polymer, the hydroxylated triglyceride oligomers in the hair care compositions show enhanced benefits in deposition, wet and dry conditioning and hair feel.

Any known natural or synthetic cationic polymer can be used herein. Examples include those polymers disclosed in U.S. Pat. No. 6,649,155; U.S. Patent Application Publication Nos. 2008/0317698; 2008/0206355; and 2006/0099167, which are incorporated herein by reference in their entirety.

The cationic polymer is included in the composition at a level from about 0.01 wt % to about 1 wt %, in one embodiment from about 0.05 wt % to about 1.0 wt %, in another embodiment from about 0.25 wt % to about 0.60 wt %, in view of providing the benefits of the hair care composition. The ratio of cationic polymer and the hydroxylated triglyceride oligomer by weight, in one embodiment range from about 1:100 to about 1:1, in another embodiment from 1:10 to about 1:2.

The cationic polymer is a water soluble polymer with a charge density from about 0.5 milliequivalents per gram to about 12 milliequivalents per gram. The cationic polymer used in the composition has a molecular weight of about 1,000 Daltons to about 100,000,000 Daltons. The cationic polymer is a low, medium, or high charge density cationic polymer.

These cationic polymers can include at least one of (a) a cationic guar polymer, (b) a cationic non-guar polymer, (c) a cationic tapioca polymer, (d) a cationic copolymer of acrylamide monomers and cationic monomers, (e) a synthetic, non-crosslinked, cationic polymer, which forms lyotropic liquid crystals upon combination with the detersive surfactant, and/or (f) cationic hydroxyethyl cellulose. Additionally, the cationic polymer can be a mixture of polymers.

(a) Cationic Guar Polymers

According to one embodiment, the cationic guar polymer has a weight average M.Wt. of less than about 1 million g/mol, and has a charge density of from about 0.1 meq/g to about 2.5 meq/g. In an embodiment, the cationic guar polymer has a weight average M.Wt. of less than 900 thousand g/mol, or from about 150 thousand to about 800 thousand g/mol, or from about 200 thousand to about 700 thousand g/mol, or from about 300 thousand to about 700 thousand g/mol, or from about 400 thousand to about 600 thousand g/mol.from about 150 thousand to about 800 thousand g/mol, or from about 200 thousand to about 700 thousand g/mol, or from about 300 thousand to about 700 thousand g/mol, or from about 400 thousand to about 600 thousand g/mol. In one embodiment, the cationic guar polymer has a charge density of from about 0.2 to about 2.2 meq/g, or from about 0.3 to about 2.0 meq/g, or from about 0.4 to about 1.8 meq/g; or from about 0.5 meq/g to about 1.5 meq/g.

In an embodiment, the composition comprises from about 0.01% to less than about 0.6%, or from about 0.04% to about 0.55%, or from about 0.08% to about 0.5%, or from about 0.16% to about 0.5%, or from about 0.2% to about 0.5%, or from about 0.3% to about 0.5%, or from about 0.4% to about 0.5%, of cationic guar polymer (a), by total weight of the composition.

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a M.Wt. of 500,000 g/mole. Another guar hydroxypropyltrimonium chloride with a charge density of about 1.1 meq/g and a M.Wt. of about 500,000 g/mole is available from Ashland. A further guar hydroxypropyltrimonium chloride with a charge density of about 1.5 meq/g and a M.Wt. of about 500,000 g/mole is available from Ashland.

Other suitable polymers include: Hi-Care 1000, which has a charge density of about 0.7 meq/g and a M.Wt. of about 600,000 g/mole and is available from Rhodia; N-Hance 3269 and N-Hance 3270, which have a charge density of about 0.7 meq/g and a M.Wt. of about 425,000 g/mole and is available from Ashland; AquaCat CG518 has a charge density of about 0.9 meq/g and a M.Wt. of about 50,000 g/mole and is available from Ashland. A further non-limiting example is N-Hance 3196 from Ashland.

(b) Cationic Non-Guar Polymers

The shampoo compositions of the present invention comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

The galactomannan polymer derivatives for use in the shampoo compositions of the present invention have a molecular weight from about 1,000 to about 10,000,000. In one embodiment of the present invention, the galactomannan polymer derivatives have a molecular weight from about 5,000 to about 3,000,000. As used herein, the term "molecular weight" refers to the weight average molecular weight. The weight average molecular weight may be measured by gel permeation chromatography.

The shampoo compositions of the present invention include galactomannan polymer derivatives which have a cationic charge density from about 0.9 meq/g to about 7 meq/g. In one embodiment of the present invention, the galactomannan polymer derivatives have a cationinc charge density from about 1 meq/g to about 5 meq/g. The degree of substitution of the cationic groups onto the galactomannan structure should be sufficient to provide the requisite cationic charge density.

(c) Cationically Modified Starch Polymer

The shampoo compositions of the present invention comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions of the present invention comprise cationically modified starch polymers at a range of about 0.01% to about 10%, and more preferably from about 0.05% to about 5%, by weight of the composition.

Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof. Tapioca starch is preferred.

In one embodiment of the present invention, cationically modified starch polymers are selected from degraded cationic maize starch, cationic tapioca, cationic potato starch, and mixtures thereof. In another embodiment, cationically modified starch polymers are cationic corn starch and cationic tapioca. Cationic tapioca starch is preferred.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starch, guar, cellulose, cassia, locust bean, konjac, tara, galactomannan, and tapioca. In a further embodiment, cationic deposition polymers are selected from Mirapol® 100S (Rhodia), Jaguar® C17, polyqueaternium-6, cationic tapioca starch (Akzo), polyquaternium-76, and mixtures thereof.

(d) Cationic Copolymer of an Acrylamide Monomer and a Cationic Monomer

According to an embodiment of the present invention, the shampoo composition comprises a cationic copolymer of an acrylamide monomer and a cationic monomer, wherein the copolymer has a charge density of from about 1.0 meq/g to about 3.0 meq/g. In an embodiment, the cationic copolymer is a synthetic cationic copolymer of acrylamide monomers and cationic monomers.

In an embodiment, the cationic copolymer (b) is AM:TRIQUAT which is a copolymer of acrylamide and 1,3-Propanediaminium,N-[2-[[[dimethyl[3-[(2-methyl-1-oxo-2-propenyl)amino]propyl]ammonio]acetyl]amino]ethyl]2-hydroxy-N,N,N',N',N'-pentamethyl-, trichloride. AM:TRIQUAT is also known as polyquaternium 76 (PQ76). AM:TRIQUAT may have a charge density of 1.6 meq/g and a M.Wt. of 1.1 million g/mol.

In an embodiment, the cationic copolymer is a trimethylammoniopropylmethacrylamide chloride-N-Acrylamide copolymer, which is also known as AM:MAPTAC. AM:MAPTAC may have a charge density of about 1.3 meq/g and a M.Wt. of about 1.1 million g/mol. In an embodiment, the cationic copolymer is AM:ATPAC. AM:ATPAC may have a charge density of about 1.8 meq/g and a M.Wt. of about 1.1 million g/mol.

(e) Cationic Synthetic Polymer

The cationic polymer described herein aids in providing damaged hair, particularly chemically treated hair, with a surrogate hydrophobic F-layer. Lyotropic liquid crystals are formed by combining the synthetic cationic polymers described herein with the aforementioned anionic detersive surfactant component of the shampoo composition. The synthetic cationic polymer has a relatively high charge density. It should be noted that some synthetic polymers having a relatively high cationic charge density do not form lyotropic liquid crystals, primarily due to their abnormal linear charge densities. Such synthetic cationic polymers are described in WO 94/06403 to Reich et al.

The concentration of the cationic polymers ranges about 0.025% to about 5%, preferably from about 0.1% to about 3%, more preferably from about 0.2% to about 1%, by weight of the shampoo composition.

The cationic polymers have a cationic charge density of from about 2 meq/gm to about 7 meq/gm, preferably from about 3 meq/gm to about 7 meq/gm, more preferably from about 4 meq/gm to about 7 meq/gm. In some embodiments, the cationic charge density is about 6.2 meq/gm. The polymers also have a molecular weight of from about 1,000 to about 5,000,000, more preferably from about 10,000 to about 2,000,000, most preferably 100,000 to about 2,000,000. where X-=halogen, hydroxide, alkoxide, sulfate or alkylsulfate.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride (DADMAC).

Nonlimiting examples of cationic monomers comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Nonlimiting examples of cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride. Nonlimiting examples of cationic monomers include trimethyl ammonium propyl (meth)acrylamido chloride.

(f) Cationically Modified Hydroxyethyl Cellulose Polymer

The hair care compositions of the present invention may comprise cationically modified hydroxyethyl cellulose polymers. The cationic cellulosic polymers can further include hydrophobes to adjust polymer hydrophobicity. Non-limiting examples may include polyquaternium-10 of quaternized hydroxyethyl cellulose, such as UCARE™ Polymer LR-30M, JR-30M and KG-30M and UCARE™ Extreme Polymer from Dow.

In many embodiments, the mixture of the cationic polymers in the hair care composition are binary and ternary. The ratio of the binary mixture in weight ranges from about 1:10 to 10:1. A binary mixture example include a mixture of DADMAC and UCARE™ Polymer KG-30M with a ratio of 1:1.

2. Benefit Agents

In an embodiment, the hair care composition further comprises one or more additional benefit agents. The benefit agents comprise a material selected from the group consisting of anti-dandruff agents, vitamins, lipid soluble vitamins, chelants, perfumes, brighteners, enzymes, sensates, attractants, anti-bacterial agents, dyes, pigments, bleaches, and mixtures thereof.

In one aspect said benefit agent may comprise an anti-dandruff agent. Such anti-dandruff particulate should be physically and chemically compatible with the components of the composition, and should not otherwise unduly impair product stability, aesthetics or performance.

According to an embodiment, the hair care composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt.

Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt % to about 5 wt %, or from about 0.1 wt % to about 3 wt %, or from about 0.1 wt % to about 2 wt %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753,196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is is included in an amount of from about 0.01 wt % to about 5 wt %, or from about 0.1 wt % to about 3 wt %, or from about 0.3 wt % to about 2 wt %. In an embodiment, the azole anti-microbial active is ketoconazole. In an embodiment, the sole anti-microbial active is ketoconazole.

Embodiments of the hair care composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001 wt % to about 10 wt %, or from about 0.01 wt % to about 7 wt %, or from about 0.1 wt % to about 5 wt % of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, PC, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999,38,4211-6). In an embodiment, the ZLM is a hydroxy double salt conforming to the formula $[M^{2+}_{1-x}M^{2+}_{1+x}(OH)_{3(1-y)}] + A^{n-}_{(1=3y(/n)} \cdot nH_2O$ where the two metal ions ($M^{2+}$) may be the same or different. If they are the same and represented by zinc, the formula simplifies to $[Zn_{1+x}(OH)_2]^{2x+}2x\ A^- \cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Embodiments of the hair care composition may also comprise fatty alcohol gel networks, which have been used for years in cosmetic creams and hair conditioners. These gel networks are formed by combining fatty alcohols and surfactants in the ratio of about 1:1 to about 40:1 (alternatively from about 2:1 to about 20:1, and alternatively from about 3:1 to about 10:1). The formation of a gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network. The gel network contributes a stabilizing benefit to cosmetic creams and hair conditioners. In addition, they deliver conditioned feel benefits for hair conditioners.

Thus according to an embodiment, the fatty alcohol is included in the fatty alcohol gel network at a level by weight of from about 0.05 wt % to about 14 wt %. For example, the fatty alcohol may be present in an amount ranging from about 1 wt % to about 10 wt %, and alternatively from about 6 wt % to about 8 wt %.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20, are suitable.

In some embodiments, the compositions of the present invention may be free of sulfates, free of silicones, mineral oil, dye and/or free of parabens.

The following is an optional way to prepare a gel network in a shampoo: A vessel is charged with water and the water is heated to about 74° C. Cetyl alcohol, stearyl alcohol, and SLES surfactant are added to the heated water. After incorporation, the resulting mixture is passed through a heat exchanger where the mixture is cooled to about 35° C. Upon cooling, the fatty alcohols and surfactant crystallized to form a crystalline gel network. Table 2 provides the components and their respective amounts for the gel network composition.

TABLE 2

| Gel network components | |
|---|---|
| Ingredient | Wt. % |
| Water | 78.27% |
| Cetyl Alcohol | 4.18% |
| Steary Alcohol | 7.52% |
| Sodium laureth-3 sulfate (28% Active) | 10.00% |
| 5-Chloro-2-methyl-4-isothiazolin-3-one, Kathon CG | 0.03% |

3. Stabilizing Agents

In an embodiment, the hair care composition further comprises one or more stabilizing agents.

The stabilizing agents comprise a material selected from the groups consisting of polymeric thickeners, platelets or crystalline powders. The exemplary stabilizing agents include, but are not limited to, acrylic crosslinked polymers such as acrylate copolymers having the trade name Rheocare TTA from BASF, ethylene glycol distearate (EGDS) from Galaxy Surfactants, polyquaternium-10 having a trade name UCARE EP from Dow, and/or hydrogenated castor oil having the trade name Thixcin R from Elementis Specialties. The concentration of the stabilizing agents in the hair care compositions ranges from about 0.01% to about 5%.

EXAMPLES

The following examples illustrate the present invention. The exemplified compositions can be prepared by conventional formulation and mixing techniques. It will be appreciated that other modifications of the hair care composition within the skill of those in the hair care formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

TABLE 3

Solvent carrier examples

| | Comparative | | | Inventive | | | | | |
|---|---|---|---|---|---|---|---|---|---|
| | A | B | C | D | E | F | G | H | I |
| Material | 9[1] | 10[2] | 11[3] | 1[4] | 2[5] | 6[6] | 7[7] | 3[8] | 4[9] |
| Repeat unit | M | M | O | O | O | O | O | O | O |
| Sidechain FA | Oleic | | — | | Ricinoleic and Stearic | | | Oleic | |
| Charge | — | — | — | — | — | — | Cationic | — | — |

All exemplary compositions above contain 0.15 wt % of comparative or inventive example in Hexane.

Key
M: Castor oil monomer
O: Castor oil oligomer

Ingredient Key
[1]Material 9, Fatty acid modified castor oil from Momentive
[2]Material 10, Fatty acid modified castor oil from Momentive
[3]Material 11, Crodabond ™ CSA, Hydrogenated Castor Oil/Sebacic Acid Copolymer from Croda
[4]Material 1, poly fatty acid based nonionic castor oil derivative from Momentive
[5]Material 2, poly fatty acid based nonionic castor oil derivative from Momentive
[6]Material 6, poly fatty acid based quaternary ammonium compound from Momentive
[7]Material 7, poly fatty acid based quaternary ammonium compound from Momentive
[8]Material 3, poly fatty acid based nonionic castor oil derivative from Momentive
[9]Material 4, poly fatty acid based nonionic castor oil derivative from Momentive

TABLE 4

Shampoo examples

| | Comparative | | Inventive | | | | | | | | | |
|---|---|---|---|---|---|---|---|---|---|---|---|---|
| | J | K | L | M | N | O | P | Q | R | S | T | U |
| Water[1] | q.s. | q.s. | q.s. | q.s. | q.s. | q.s. | q.s. | q.s. | q.s. | q.s. | q.s. | q.s. |
| Sodium Lauroyl Sarcosinate[2] | 4.0 | 4.0 | 4.0 | 4.0 | 4.0 | 4.0 | 4.0 | 4.0 | 4.0 | 4.0 | 4.0 | 4.0 |
| Sodium Cocoyl Isethionate[3] | 6.0 | 6.0 | 6.0 | 6.0 | 6.0 | 6.0 | 6.0 | 6.0 | 6.0 | 6.0 | 6.0 | 6.0 |
| Lauramidopropyl Betaine[4] | 9.7 | 9.7 | 9.7 | 9.7 | 9.7 | 9.7 | 9.7 | 9.7 | 9.7 | 9.7 | 9.7 | 9.7 |
| Polyquaternium-10 LR30M[5] | 0.6 | 0.6 | 0.6 | 0.6 | 0.6 | 0.6 | 0.6 | 0.6 | 0.6 | | | |
| Polyquaternium-10 JR30M[6] | | | | | | | | | | 0.25 | 0.25 | 0.25 |
| Acrylates copolymer[7] | 0.7 | 0.7 | 0.7 | 0.7 | 0.7 | 0.7 | 0.7 | 0.7 | 0.7 | | | |
| EGDS[8] | | | | | | | | | | 2.2 | 2.2 | 2.2 |
| Material 7[9] | | | 1.0 | 0.5 | 0.25 | | | | | 1.0 | | |
| Material 5[10] | | | | | | 1.0 | | | | | 1.0 | |
| Material 3[11] | | | | | | | 1.0 | | | | | 1.0 |
| Material 6[12] | | | | | | | | 1.0 | | | | |
| Material 1[13] | | | | | | | | | 1.0 | | | |
| Material 11[14] | | 1.0 | | | | | | | | | | |
| Fragrance, preservatives, pH, viscosity adjustment | Up to 5% | Up to 5% | Up to 5% | Up to 5% | Up to 5% | Up to 5% | Up to 5% | Up to 5% | Up to 5% | Up to 5% | Up to 5% | Up to 5% |

Ingredient Key
[1]Water, DI water from Misty Mountain Spring water
[2]Sodium Lauroyl Sarcosinate, SP Crodasinic LS30/NP MBAL-LQ-(RB) from Croda
[3]Sodium Cocoyl Isethionate, PUREACT I-85 E-HA Flakes from innospec
[4]Lauramidopropyl Betaine, Mackam DAB ULS from Salvay USA Inc.
[5]Polyquaternium-10, UCARE ™ Polymer LR-30M from Amerchol
[6]Polyquaternium-10, UCARE ™ Polymer JR-30M from Amerchol
[7]Acrylates copolymer, Rheocare TTA from BASF
[8]EGDS, Ethylene glycol distearate from Galaxy Surfactants
[9]Material 7, poly fatty acid based quaternary ammonium compound from Momentive
[10]Material 5, poly fatty acid based nonionic castor oil derivative from Momentive
[11]Material 3, poly fatty acid based nonionic castor oil derivative from Momentive
[12]Material 6, poly fatty acid based quaternary ammonium compound from Momentive
[13]Material 1, poly fatty acid based nonionic castor oil derivative from Momentive
[14]Material 11, Crodabond ™ CSA, Hydrogenated Castor Oil/Sebacic Acid Copolymer from Croda

TABLE 5

Rinse off conditioner

| | Comparative | | Inventive | | | | | | |
|---|---|---|---|---|---|---|---|---|---|
| | V | W | X | Y | Z | AA | BB | CC | EE |
| Water[1] | q.s. | q.s. | q.s. | q.s. | q.s. | q.s. | q.s. | q.s. | q.s. |
| Behentrimonium Methosulfate/Isopropyl alcohol[2] (BTMS) | 3.0 | 3.0 | 3.0 | 3.0 | 3.0 | 3.0 | 3.0 | 3.0 | 3.0 |
| Cetyl Alcohol[3] | 1.2 | 1.2 | 1.2 | 1.2 | 1.2 | 1.2 | 1.2 | 1.2 | 1.2 |
| Stearyl Alcohol[4] | 2.9 | 2.9 | 2.9 | 2.9 | 2.9 | 2.9 | 2.9 | 2.9 | 2.9 |
| Material 1[5] | | | 1.0 | 2.0 | 4.0 | 1.0 | | | |
| Material 7[6] | | | | | | | 1.0 | | |
| Material 5[7] | | | | | | | | 1.0 | |
| Material 3[8] | | | | | | | | | 1.0 |
| Material 11[9] | 1.0 | 2.0 | | | | | | | |
| Aminosilicone[10] | | | | | | 1.0 | | | |
| Fragrance, preservatives, pH, viscosity adjustment | Up to 5% | Up to 5% | Up to 5% | Up to 5% | Up to 5% | Up to 5% | Up to 5% | Up to 5% | Up to 5% |

Ingredient Key
[1]Water, DI water from Misty Mountain Spring water
[2]Behentrimonium Methosulfate/Isopropyl alcohol (BTMS)
[3]Cetyl Alcohol, CO-1698PT from P&G Chemicals
[4]Stearyl Alcohol, CO-1899 from P&G Chemicals
[5]Material 1, poly fatty acid based nonionic castor oil derivative from Momentive
[6]Material 7, poly fatty acid based quaternary ammonium compound from Momentive
[7]Material 5, poly fatty acid based nonionic castor oil derivative from Momentive
[8]Material 3, poly fatty acid based nonionic castor oil derivative from Momentive
[9]Material 11, Crodabond ™ CSA, Hydrogenated Castor Oil/Sebacic Acid Copolymer from Croda
[10]Y-14945 from Momentive

TABLE 6

Leave-on conditioner examples

| | Comparative | | Inventive | | | | |
|---|---|---|---|---|---|---|---|
| | FF | GG | HH | II | JJ | KK | LL |
| Water purified[1] | q.s. | q.s. | q.s. | q.s. | q.s. | q.s. | q.s. |
| Hydoxyethylcellulose[2] | 0.5 | 0.5 | 0.5 | 0.5 | 0.5 | 0.5 | 0.5 |
| Behenamidopropyl Dimethylamine[3] | 0.9 | 0.9 | 0.9 | 0.9 | 0.9 | 0.9 | 0.9 |
| Cetyl Alcohol[4] | 0.8 | 0.8 | 0.8 | 0.8 | 0.8 | 0.8 | 0.8 |
| Stearyl Alcohol[5] | 0.5 | 0.5 | 0.5 | 0.5 | 0.5 | 0.5 | 0.5 |
| Glyceryl Stearate[6] | 0.2 | 0.2 | 0.2 | 0.2 | 0.2 | 0.2 | 0.2 |
| Hexanediol and Caprylyl Glycol[7] | 0.4 | 0.4 | 0.4 | 0.4 | 0.4 | 0.4 | 0.4 |
| Material 1[8] | | | 2.0 | 1.0 | 0.5 | | 0.5 |
| Material 7[9] | | | | | | 1.0 | |
| Aminosilicone[10] | | | | | | | 0.5 |
| Material 11[11] | 0.5 | 1.0 | | | | | |
| Fragrance, preservatives, pH, viscosity adjustment | Up to 5% | Up to 5% | Up to 5% | Up to 5% | Up to 5% | Up to 5% | Up to 5% |

Ingredient Key
[1]Water, DI water from Misty Mountain Spring water
[2]Hydroxy Cellulose, Natrosol ™ 250HHR CS from Ashland
[3]INCROMINE ™ BD-PA-(MH) from Croda
[4]Stearamidopropyl Dimethylamine (HA162), SP POLAWAX NF MBAL-PA-(RB) from Croda
[5]Cetyl Alcohol, CO-1698PT from P&G Chemicals
[6]Stearyl Alcohol, CO-1899 from P&G Chemicals
[7]Symdiol ® 68 from Symrise
[8]Material 1, poly fatty acid based nonionic castor oil derivative from Momentive
[9]Material 7, poly fatty acid based quaternary ammonium compound from Momentive
[10]Aminosilicone, Y-14945 from Momentive
[11]Material 11, Crodabond ™ CSA, Hydrogenated Castor Oil/Sebacic Acid Copolymer from Croda

TABLE 7

Leave on conditioner formula

| | Comparative | | Inventive | | | | |
|---|---|---|---|---|---|---|---|
| | MM | NN | OO | PP | QQ | SS | TT |
| Water purified[1] | q.s. | q.s. | q.s. | q.s. | q.s. | q.s. | q.s. |
| Hydroxy Cellulose[2] | 0.4 | 0.4 | 0.4 | 0.4 | 0.4 | 0.4 | 0.4 |
| Polyox WSR N-10 PEG 2M[3] | 0.27 | 0.27 | 0.27 | 0.27 | 0.27 | 0.27 | 0.27 |
| Quaternium-18[4] | 0.4 | 0.4 | 0.4 | 0.4 | 0.4 | 0.4 | 0.4 |
| Stearamidopropyl Dimethylamine[5] | 0.54 | 0.54 | 0.54 | 0.54 | 0.54 | 0.54 | 0.54 |
| Cetearyl Alcohol & Polysorbate 60[5] | 0.27 | 0.27 | 0.27 | 0.27 | 0.27 | 0.27 | 0.27 |
| Cetyl Alcohol[6] | 0.5 | 0.5 | 0.5 | 0.5 | 0.5 | 0.5 | 0.5 |
| Stearyl Alcohol[7] | 0.35 | 0.35 | 0.35 | 0.35 | 0.35 | 0.35 | 0.35 |
| Glyceryl Stearate[8] | 0.14 | 0.14 | 0.14 | 0.14 | 0.14 | 0.14 | 0.14 |
| Oley Alcohol[9] | 0.14 | 0.14 | 0.14 | 0.14 | 0.14 | 0.14 | 0.14 |
| Material 1[10] | | | 2.0 | 1.0 | 0.5 | | 0.5 |
| Material 7[11] | | | | | | 1.0 | |
| Aminosilicone[12] | | | | | | | 0.5 |
| Crodabond[13] | 0.5 | 1.0 | | | | | |
| Preservatives, pH, viscosity adjustment | Up to 5% | Up to 5% | Up to 5% | Up to 5% | Up to 5% | Up to 5% | Up to 5% |

Ingredient Key
[1]Water, DI water from Misty Mountain Spring water
[2]Hydroxy Cellulose, Natrosol™ 250HHR CS from Ashland
[3]Polyox WSR N-10 PEG 2M, from Amerchol
[4]Quaternium-18, VARISOFT 442 100 P from Evonik
[5]Stearamidopropyl Dimethylamine (HA162), SP POLAWAX NF MBAL-PA-(RB) from Croda
[6]Cetyl Alcohol, CO-1698PT from P&G Chemicals
[7]Stearyl Alcohol, CO-1899 from P&G Chemicals
[8]Glyceryl Stearate, HALLSTAR® GMS PURE from Hallstar
[9]Oley Alcohol, HD-Ocenol® 90/95 V from BASF
[8]Material 1, poly fatty acid based nonionic castor oil derivative from Momentive
[9]Material 7, poly fatty acid based quaternary ammonium compound from Momentive
[10]Aminosilicone, Y-14945 from Momentive
[11]Crodabond™ CSA, Hydrogenated Castor Oil/Sebacic Acid Copolymer from Croda

TABLE 8

Dual phase leave on treatment formula

| | Comparative | Inventive | | |
|---|---|---|---|---|
| | UU | VV | WW | XX |
| Phase A-Water Phase | | | | |
| Water Purified[1] | q.s | q.s | q.s | q.s |
| Polyimide-1[2] | 4.0 | 4.0 | 4.0 | 4.0 |
| Polysorbate 20[3] | 0.5 | 0.5 | 0.5 | 0.5 |
| Polyquaterium-6[4] | 0.6 | 0.6 | 0.6 | 0.6 |
| Preservatives, pH, viscosity adjustment | Up to 5% | Up to 5% | Up to 5% | Up to 5% |
| Phase B-Oil phase | | | | |
| Isododecane[5] | 25.0 | 25.0 | 25.0 | 25.0 |
| Diisopropyl Adipate[6] | 5.0 | 5.0 | 5.0 | 5.0 |
| Crodaband[7] | 2.0 | — | — | — |
| Material 7[8] | — | 2.0 | — | — |
| Material 1[9] | — | — | 2.0 | — |
| Material 5[10] | — | — | — | 2.0 |

Ingredient Key
[1]Water, DI water from Misty Mountain Spring water
[2]Polyimide-1, AQUAFLEX XL-30 from Ashland
[3]Polysorbate 20, TWEEN™ 80-LQ-(AP) from Croda
[4]Polyquaterium-6, Genamin PDAC from Clariant
[5]Isododecane, Permethyl 99A from Presperse
[6]Diisopropyl Adipate, SCHERCEMOL™ DIA ESTER from Lubrizol
[7]Crodabond™ CSA, Hydrogenated Castor Oil/Sebacic Acid Copolymer from Croda
[8]Material 7, poly fatty acid based quaternary ammonium compound from Momentive
[9]Material 1, poly fatty acid based nonionic castor oil derivative from Momentive
[10]Material 5, poly fatty acid based nonionic castor oil derivative from Momentive The hair care composition may be presented in typical hair care formulations. They may be in the form of solutions, dispersion, emulsions, powders, talcs, encapsulated spheres, spongers, solid dosage forms, foams, and other delivery mechanisms. The compositions of the embodiments of the present invention may be hair tonics, leave-on hair products such as treatment and styling products, rinse-off hair products such as shampoos, and any other form that may be applied to hair.

According to one embodiment, the hair care compositions may be provided in the form of a porous, dissolvable solid structure, such as those disclosed in U.S. Patent Application Publication Nos. 2009/0232873; and 2010/0179083, which are incorporated herein by reference in their entirety. As described in these references, such dissolvable solid structure embodiments will typically have a water content well below at least about 20% aqueous carrier element of certain embodiments described above. In a solid substrate, the weight percentage of the hydroxylated triglyceride oligomer in the dissolvable solid structure is from about 5 to about 60, more preferably from about 10 to 40.

The hair care compositions are generally prepared by conventional methods such as those known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

The hydroxylated triglyceride oligomers in the hair care composition can be dispersed as discrete particles or dissolved in a liquid carrier, as well as mixed in a solid substrate. The particle size of the discrete particles ranges from about 0.01 µm to about 50 µm, more preferably from about 0.05 µm to about 30 µm. The discrete particles can be pre-emulsified prior to the addition to the hair care compositions. The pre-emulsions include cationic, nonionic, and anionic emulsions with emulsifiers described in G. Additional Components. The particle size of the pre-emulsions range is targeted to achieve the particle sizes in the hair care compositions. The ratio of emulsifier and hydroxylated triglyceride oligomer by weight in the pre-emulsion range from about 0.01 to about 1.0, more preferably from about 0.04 to about 0.4. The pH of the hair care composition is from about 3 to about 8, more preferably from about 4.5 to 7.

Test Methods

It is understood that the test methods that are disclosed in the Test Methods Section of the present application should be used to determine the respective values of the parameters of Applicants' invention as such invention is described and claimed herein.

Viscosity Measurement

The viscosity properties of the hydroxylated triglyceride oligomer and comparative compound are measured on a stress-controlled rheometer, such as the TA Discovery HR-3 hybrid rheometer by TA Instrument, using 40 millimeter stainless steel parallel plates with 1 millimeter gap. About 1 mL of a sample is placed onto the lower plate. The excess material is trimmed using a plastic flat edge ensuring that material is not sheared by movements of the plates. The conditioning step is operated with a soak time of 10.0 second at 25° C. Preshear rate is set at 10 l/s with duration of 10.0 second. The flow-sweep step is run logarithmically between 0.01 and 1000 l/s of shear rate. Data is is collected at 10 points/decade in log mode. Viscosity (Pa·s.) at shear rate of 1 l/s is used.

Leave on Treatment Protocol

A moderately oxidatively-damaged Caucasian hair switch with weight of 4g and length of 8 inches is first washed with a clarifying shampoo (see shampoo washing protocol below) and allowed to air dry for 24 hours. An amount of 500 ppm of a hydroxylated triglyceride oligomer or a comparative example formulated in a carrier is thoroughly spread on the hair switch. The treatment is repeated to two additional switches. The treated hair switches are allowed to dry and equilibrate overnight under controlled temperature and relative humidity conditions (27° C. and 50% RH).

Shampoo Treatment

A moderately oxidatively-damaged Caucasian hair switch with weight of 4 g and length of 8 inches is first wetted with warm water for 30 seconds. An amount of 0.10 g of shampoo per gram of a hair switch is spread via a syringe onto separate hair switch. Each application consists of adding the shampoo to the hair, milking for 30 seconds followed by rinsing for 30 seconds. The treatment is repeated to two additional switches. The treated hair switches are allowed to dry and equilibrate overnight under controlled temperature and relative humidity conditions (27° C. and 50% RH).

Rinse Off Conditioner Treatment

A moderately oxidatively-damaged Caucasian hair switch with weight of 4 g and length of 8 inches is first washed with a clarifying shampoo (see shampoo washing protocol above). After rinseing, an amount of 0.10 g of conditioner per gram of a hair switch is spread via a syringe onto the hair switch. Each application consists of adding the conditioner to the hair, milking for 30 seconds followed by rinsing for 30 seconds. The treatment is repeated to two additional switches. The treated hair switches are allowed to dry and equilabrited overnight under controlled temperature and relative humidity conditions (27° C. and 50% RH).

Dry Combing Tests

This combing test determines the amount of friction on the hair provided by the hair care composition as measured by the force required to move a comb through a moderately oxidatively-damaged Caucasian hair switch with weight of 4 g and length of 8 inches. This method emulates the motion of combing hair from the root to tip of the treated hair switch. The operator ranks and balances the 4 g, 8 in. hair switches for base line condition by using an Instron machine. The operator then applies a measured amount of the hair care composition to a hair switch (0.1 g/g hair), distributes the product evenly through the switch, and rinses as per the protocol. Wet switches are evaluated for friction and then allowed to dry overnight and evaluated the next day for friction force using the Instron machine. Each test product is applied to a total of 3 switches. The data is then analyzed using standard statistical methods. The combing force is measured for each switch and an average for the three switches is calculated. Lower friction forces are better for hair detangling.

Shampoo In-Lab Screening

A moderately oxidatively-damaged Caucasian hair switch with weight of 20 g and length of 10 inches is washed by an expert panelist (see shampoo washing protocol above). The expert panelist gives a score of 0-5 for wet and dry attributes. Two additional expert panelists repeat the protocol by treating a separate hair switch. The score is the average from three expert panelists. A control treatment without the hydroxylated triglyceride oligomer or exemplary comparative compound is also tested. Expert evaluation scores are calculated with the formula below. Higher scores are better.

Expert evaluation scores=(average score−control score)*100

Comparative Data

Using the abovementioned test protocols, the wet and dry conditioning benefits of selected formulations were measured. The data in Table 9 and Table 10 reflect improved dry conditioning benefit provided by leave on treatment compositions containing the hydroxylated triglyceride oligomers described herein. Data in Table 11 demonstrate that the described hydroxylated triglyceride oligomers provided wet and dry conditioning improvements in sulfate free shampoo formulations versus comparative examples. The data in Table 12 show that the described hydroxylated triglyceride oligomers provide significantly lower hair friction in dry conditioning in rinse off conditioners versus comparative examples.

TABLE 9

| | Comparative | | | Inventive | | | | | |
|---|---|---|---|---|---|---|---|---|---|
| | A | B | C | D | E | F | G | H | I |
| Material | 9 | 10 | 11 | 1 | 2 | 6 | 7 | 3 | 4 |
| Viscosity, Pa·s @ 1 s$^{-1}$ | 0.3 | 0.6 | 48.5 | 5.0 | 2.8 | 15.1 | 1.9 | 2.2 | 2.8 |
| Combing force, mean (grams-force) | 243 | 225 | 173 | 120 | 141 | 136 | 122 | 117 | 120 |
| Standard error, gf | 38 | 34 | 23 | 13 | 18 | 20 | 16 | 15 | 20 |

TABLE 10

| | Comparative GG | | Inventive II | |
|---|---|---|---|---|
| | Mean (grams-force) | Standard error (grams-force) | Mean (grams-force) | Standard error (grams-force) |
| Dry friction at tip | 55 | 1.8 | 43 | 1.8 |
| Dry friction in mid | 14.9 | 0.23 | 12.7 | 0.21 |

TABLE 11

| | Comparative | Inventive | | |
|---|---|---|---|---|
| Expert evaluation scores | K | L | Q | R |
| Ease of lathering | −13 | 88 | 13 | 25 |
| Wet moisturized/soft feel | 113 | 163 | 138 | 150 |
| Dry ease of combing (body) | 13 | 100 | 113 | 50 |
| Dry ease of combing (tip) | 100 | 163 | 138 | 125 |
| Dry smooth feel (body) | 38 | 38 | 125 | 100 |
| Dry smooth feel (tip) | 50 | 63 | 113 | 75 |
| Dry clean feel | 25 | 50 | 38 | 38 |

TABLE 12

| | Comparative V | | Inventive X | |
|---|---|---|---|---|
| | Mean (grams-force) | Standard error (grams-force) | Mean (grams-force) | Standard error (grams-force) |
| Dry friction at tip | 59 | 2.7 | 52 | 2.1 |
| Dry friction in mid | 11.7 | 0.14 | 8.0 | 0.34 |

EXAMPLES/COMBINATIONS

A. A hair care composition comprising:
  a) from about 0.01% to about 15%, by weight of said hair care composition, of a hydroxylated triglyceride oligomer comprising:
    (i.) at least two hydroxylated triglyceride repeating units, wherein the hydroxylated triglyceride repeating units comprise one or more hydroxyl groups; and
    (ii.) at least one fatty acid esterified with at least one of the hydroxyl groups in the hydroxylated triglyceride oligomer and
    wherein the oligomer has a viscosity of from 1 to 30 Pa·s; and
  b) a vehicle having one or more of the following components, by weight of said hair care composition,
    (i.) an aqueous carrier;
    (ii.) from about 5% to about 50% of one or more anionic surfactants in an aqueous carrier;
    (ii.) a gel matrix phase in an aqueous carrier comprising, by weight of said hair care composition:
      1) from about 0.1% to about 20% of one or more high melting point fatty compounds;
      2) from about 0.1% to about 10% of a cationic surfactant system;
    (iii.) from about 0.1% to 20% of a nonionic surfactant in an aqueous carrier;
    (iv.) from about 20% to about 99.99% of solvent carrier.

B. The composition of paragraph A, wherein the hydroxylated triglyceride oligomer comprises ricinoleic or lesquerolic triglyceride.

C. The composition of any one of paragraphs A or B, wherein the oligomer further comprises at least one quaternary ammonium group.

D. The composition of any one of paragraphs A to C, wherein the hydroxylated triglyceride oligomer has repeating units of from about 2 to about 6.

E. The composition of any one of paragraphs A to D, wherein the at least one fatty acid is esterified with each hydroxyl group in the hydroxylated triglyceride oligomer.

F. The composition of any one of paragraphs A to E, wherein the fatty acid esters of the hydroxylated triglyceride oligomer are esterified with fatty acids selected from the group consisting of ricinoleic acid, oleic acid, stearic acid, 12-hydroxy stearic acid and mixtures thereof.

G. The composition of paragraph A, wherein the hydroxylated triglyceride oligomer is oligomerized with a diacid.

H. The composition of paragraph G, wherein the diacid contains four carbons.

I. The composition of any one of paragraphs A to H, wherein the fatty acid esters of the hydroxylated triglyceride oligomer have a terminal ester of oleic acid or stearic acid.

J. The composition of paragraph C, wherein at least one of the quaternary ammonium groups is from a protonated amino group in the hydroxylated triglyceride oligomer.

K. The composition of paragraph C, wherein the oligomer comprises from 2 to about 6 quaternary ammonium groups.

L. The composition of paragraph C, wherein the quaternary ammonium group in the oligomer has a counter ion, and the counter ion is chloride or a fatty acid.

M. The composition of paragraph L, wherein the counter ion of the quaternary ammonium group in the hydroxylated triglyceride oligomer is stearic acid or oleic acid.

N. The composition of paragraph C, wherein the quaternary ammonium groups are connected with hydrocarbon and polyether linkages.

O. The composition of paragraph N, wherein all the hydroxylated triglyceride repeating units are linked to the quaternary ammonium group.

P. The composition of any one of paragraphs A to 0, wherein the viscosity of the hydroxylated triglyceride oligomer is about from 2 to about 25 Pa·s.

Q. The composition of any one of paragraphs A to P, wherein the surfactant is a sulfate-free surfactant.

R. The composition of any one of paragraphs A to P, wherein the solvent carrier is a hydrocarbon or an alcohol.

S. The composition of any one of paragraphs A to R, wherein the composition is silicone-free.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising:
   a) about 0.01% to about 15%, by weight of said hair care composition, of a triglyceride oligomer comprising:
      (i) at least two triglyceride repeating units linked to each other by an ester linkage; and
      (ii) at least one fatty acid esterified with at least one of the triglyceride repeating units,
         wherein the oligomer has a viscosity of 1 to 30 Pa·s; and
   b) a vehicle having one or more of the following components, by weight of said hair care composition,
      (i) an aqueous carrier;
      (ii) about 5% to about 50% of one or more anionic surfactants in an aqueous carrier;
      (iii) a gel matrix phase in an aqueous carrier comprising, by weight of said hair care composition:
         1) about 0.1% to about 20% of one or more high melting point fatty compounds;
         2) about 0.1% to about 10% of a cationic surfactant system;
      (iv) about 0.1% to 20% of a nonionic surfactant in an aqueous carrier;
      (v) about 20% to about 99.99% of solvent carrier.

2. The composition of claim 1, wherein the triglyceride oligomer is derived from castor oil or lesquerella oil.

3. The composition of claim 1, wherein the oligomer further comprises at least one quaternary ammonium group.

4. The hair care composition of claim 3, wherein at least one of the quaternary ammonium groups is from a protonated amino group in the hydroxylated triglyceride oligomer.

5. The hair care composition of claim 3, wherein the oligomer comprises from 2 to about 6 quaternary ammonium groups.

6. The hair care composition of claim 3, wherein the quaternary ammonium group in the oligomer has a counter ion, and the counter ion is chloride or a fatty acid.

7. The hair care composition of claim 6, wherein the counter ion of the quaternary ammonium group in the hydroxylated triglyceride oligomer is stearic acid or oleic acid.

8. The hair care composition of claim 3, wherein the quaternary ammonium groups are connected with hydrocarbon and polyether linkages.

9. The hair care composition of claim 8, wherein all the hydroxylated triglyceride repeating units are linked to the quaternary ammonium group.

10. The hair care composition of claim 1, wherein the triglyceride oligomer has 2 to 6 repeating units.

11. The hair care composition of claim 1, wherein the fatty acid selected from ricinoleic acid, oleic acid, stearic acid, 12-hydroxy stearic acid and mixtures thereof.

12. The hair care composition of claim 1, wherein the ester linkage comprises a reaction product of a hydroxyl group on the triglyceride repeating unit and a diacid.

13. The hair care composition of claim 12, wherein the diacid contains four carbons.

14. The hair care composition of claim 1, wherein the fatty acid is part of a chain of fatty acids that has a terminal ester of oleic acid or stearic acid.

15. The hair care composition of claim 1, wherein the viscosity of the hydroxylated triglyceride oligomer is about 2 to about 25 Pa·s.

16. The hair care composition of claim 1, wherein the surfactant is a sulfate-free surfactant.

17. The hair care composition of claim 1, wherein the solvent carrier is a hydrocarbon or an alcohol.

18. The hair care composition of claim 1, wherein the composition is silicone-free.

* * * * *